United States Patent
Hur et al.

(10) Patent No.: US 10,300,111 B2
(45) Date of Patent: May 28, 2019

(54) METHODS OF TREATING OBESITY BY ADMINISTERING A TAT PEPTIDE

(71) Applicant: Yong H. Rho, Jersey City, NJ (US)

(72) Inventors: Man-Wook Hur, Seoul (KR); Jae-Eun Kang, St. Louis, MO (US); Min-Seon Kim, Seoul (KR); Kyung-Sup Kim, Seoul (KR)

( * ) Notice: Subject to any disclaimer, the term of this patent is extended or adjusted under 35 U.S.C. 154(b) by 42 days.

(21) Appl. No.: 15/013,339

(22) Filed: Feb. 2, 2016

(65) Prior Publication Data

US 2016/0250281 A1 Sep. 1, 2016

Related U.S. Application Data

(63) Continuation of application No. 13/805,156, filed as application No. PCT/KR2009/007769 on Dec. 24, 2009, now abandoned.

(51) Int. Cl.
| | | |
|---|---|---|
| *A61K 38/16* | (2006.01) | |
| *C07K 14/005* | (2006.01) | |
| *A61K 8/64* | (2006.01) | |
| *A23L 5/00* | (2016.01) | |

(52) U.S. Cl.
CPC .......... *A61K 38/162* (2013.01); *C07K 14/005* (2013.01); *A23L 5/00* (2016.08); *A61K 8/64* (2013.01); *A61K 38/16* (2013.01); *C12N 2740/16022* (2013.01); *C12N 2740/16033* (2013.01)

(58) Field of Classification Search
None
See application file for complete search history.

(56) References Cited

U.S. PATENT DOCUMENTS

| | | |
|---|---|---|
| 2003/0215797 A1 | 11/2003 | Cohen |
| 2007/0073040 A1 | 3/2007 | Hur |

FOREIGN PATENT DOCUMENTS

| | | |
|---|---|---|
| KR | 10-0465589 B1 | 1/2005 |
| WO | 2009-130256 A2 | 10/2009 |

OTHER PUBLICATIONS

Korner et al. N. Engl. J. Med. 349(10): 926-928, 2003.*
Science. 280: 1363-1387, 1998.*
Kanasaki et al. J. Biomed. Biotech. vol. 2011, Article ID 197636, 11 pages, 2011.*
Lutz et al. Curr. Protoc. Pharmacol. Chapter: Unit 5.61, 2012.*
Saltiel Sci. Transl. Med. vol. 8, issue 323, Jan. 27, 2016, pp. 1-12.*
Daily et al., 2006, "Tat peptides inhibit neprilysin", Journal of NeuroVirology, vol. 12, pp. 153-160.

* cited by examiner

*Primary Examiner* — Christine J Saoud
(74) *Attorney, Agent, or Firm* — Riverside Law LLP

(57) ABSTRACT

The present invention relates to a composition for preventing, alleviating or treating obesity comprising a partial fragment of HIV-1 (Human Immunodeficiency Virus-1) Tat (Trans activator of transcription) protein. The peptides of the present invention induce anorexia and increase lipolysis, β-oxidation of free fatty acids, thermogenesis, and total energy expenditure, therefore may be effectively used for preventing or treating diseases related to metabolic imbalance such as obesity.

9 Claims, 23 Drawing Sheets

Specification includes a Sequence Listing.

METHODS OF TREATING OBESITY BY ADMINISTERING A TAT PEPTIDE

CROSS REFERENCE TO RELATED APPLICATIONS AND CLAIM OF PRIORITY

This application is a continuation application of U.S. application Ser. No. 13/805,156, filed Apr. 15, 2013, which is the U.S. national phase application filed under 35 U.S.C. § 371 claiming benefit to International Patent Application No. PCT/KR09/007769, filed Dec. 24, 2009, each of which applications are incorporated by reference herein in their entireties.

BACKGROUND

1. Field of the Invention

The present invention relates to a composition for preventing, alleviating or treating obesity comprising partial fragments of Tat (Trans activator of transcription).

2. Background of Technique

Wasting is a major cause of morbidity and mortality associated with Acquired Immunodeficiency Syndrome (AIDS). The present inventors investigated whether Trans activator of transcription (Tat), a protein encoded by the Human Immunodeficiency Virus 1 (HIV-1) genome, is one of the etiological agents of wasting Tat was found to have a profound effect on the reduction of adipose tissue mass and adipocyte cell size in rabbits, obese Lep−/− mice, and transgenic mice overexpressing Tat, thus demonstrating Tat's involvement in wasting. Central and peripheral administration of Tat suppressed food intake but increased thermogensis, oxygen consumption, fatty acid oxidation, and locomotor activity. Central administration of a Tat (a.a. 1-72) and Tat fragments (a.a. 20-45; a.a. 20-57) induced anorexia and weight loss. The resent inventors also mapped the domain of Tat important in weight or fat tissue reduction to a.a. 20-45. These findings suggest that Tat protein fragments can cause wasting similar to that observed in AIDS patients through increase in energy expenditure and reduction in food-intake (anorexia).

Human Immunodeficiency Virus-1 (HIV-1) is the etiological agent for Acquired Immunodeficiency Syndrome (AIDS). There are more than 40 million people infected with the HIV virus worldwide (Myers et al., 1996). Metabolic disturbances, weight loss, anorexia, and the breakdown of body tissue are major clinical consequences of HIV infection. These changes, collectively called wasting, are some of the most devastating aspects of AIDS, and are a major cause of morbidity and mortality in AIDS patients (Grunfeld et al., 1992a, b; Macallan et al., 1993, 1995).

Among the multiple mechanisms proposed, two changes that are thought to significantly contribute to wasting are an increase in resting energy expenditure and anorexia (Grunfeld et al., 1992a, b; Macallan et al., 1993). It has been suggested that these metabolic changes are mediated by the increase in cytokine levels triggered by bacterial infection (Abad et al., 2002; Grunfeld et al., 1991 and references therein; Plata-Salaman et al., 1994; Puigserver et al., 2001), but the critical candidate causing wasting in HIV-1-infected patients is unknown. Another important regulator of food intake and energy expenditure is leptin (Friedman et al., 1998). However, it was reported that serum leptin levels in patients with AIDS who were experiencing decreased food intake and weight loss, were indistinguishable from control levels (Grunfeld et al., 1996; Yarasheski et al. 1997). This result suggested that anorexia and wasting in AIDS patients is unrelated to leptin. The presence of the HIV Nef protein in the nucleus suppressed PPAR gamma expression and reduced fatty acid levels in human T and macrophage cell lines (Otake et al., 2004). Although Nef was tested in these two cell lines, the role of Nef in increased resting energy expenditure and anorexia is unknown.

Though it has been suspected that the wasting observed in HIV-1-infected patients might be related to metabolic disturbances, such as anorexia and the increased resting energy expenditure caused by the HIV-1 infection and a secondary illness, no direct causal link between HIV and metabolism has been identified (Grunfeld et al., 1992a, b; Macallan et al., 1993). In order to understand the molecular mechanism of wasting, and to develop a therapeutic method against wasting, it is important to identify the etiological agents of the process. It was assumed that the etiological agent of wasting was probably one of the viral proteins encoded by the HIV-1 genome, because infection with HIV-1 and subsequent viral replication eventually lead to wasting.

Tat is a small nuclear transcriptional activator protein encoded by the HIV-1 genome and its primary structure (amino acid sequence) is conserved in genomes of all primate lentiviruses (Myers et al., 1996). Tat is one of the most important regulators of transcription and replication of HIV-1, and plays a primary role in regulating productive and processive transcription from the HIV-1 long terminal repeat (LTR). Although full-length Tat is composed of 101 amino acids, a 72-amino-acid truncated version of Tat is sufficient to carry out most of the biological functions of full-length Tat (Jeang et al., 1999 and references therein). Tat has been shown to have multiple intracellular biological activities, such as T-lymphocyte activation, cell apoptosis, and the modulation of cellular gene expression. In addition, Tat exits from infected cells via a leaderless secretory pathway (Chang et al., 1997) and functions as an extracellular chemokine and growth factor (Jeang et al., 1999 and references therein).

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY

The present inventors have made intensive studies to develop a novel composition for preventing, alleviating or treating obesity. As results, the present inventors have discovered that partial fragments of Tat has a potent fat reducing effect by significantly reducing food-intake by activation of the central melanocortin system, and also by increasing total energy expenditure in mice and rabbits.

Accordingly, it is an object of this invention to provide a composition for preventing, alleviating or treating obesity.

Other objects and advantages of the present invention will become apparent from the following detailed description together with the appended claims and drawings.

BRIEF DESCRIPTION OF THE DRAWINGS

FIG. 1, comprising FIG. 1A indicates body weight change (kg). Rabbits were injected four times subcutaneously with control vehicle or GST-Tat protein 1 mg at two-week intervals. The rabbits were fed 200 g/day. The rabbits treated with GST-Tat weighed 380 g less at day 49.

*P<0.001 versus GST control. Average of initial body weight of control and GST-Tat treated animal group is 1.76 kg and 1.73 kg, respectively. FIG. 1B shows the average weight of various rabbit tissues: heart, kidney, lung, liver, spleen, stomach, large intestine, small intestine, abdominal and scapular fat tissue. Fat tissues were greatly reduced in size and weight. *P<0.001 versus control.

FIG. 2, comprising FIG. 2A shows photographs of the abdominal and scapular adipose tissues and adipocytes from the control vehicle and GST-Tat-treated test groups. 1, abdomen of the control rabbit; 2, abdomen of the GST-Tat-treated rabbit; 3, scapular adipose tissue of control rabbits; 4, scapular adipose tissue of GST-Tat-treated rabbits; 5, microscopic view of scapular adipocytes of control rabbit; 6, microscopic view of scapular adipocytes of a GST-Tat-treated rabbit; 7, microscopic view of abdominal adipocytes of control rabbit; 8, microscopic view of abdominal adipocytes of GST-Tat-treated rabbits; 9, cell size distribution of abdominal adipocytes; 10, cell size distribution of scapular adipocytes. Diameters (μM) of 200 adipocytes were measured using Nikon microscopy and the Image-pro 4.0 program. Adipose tissues were fixed with formaldehyde and stained with H&E (200.times. magnification). FIG. 2B shows scanning electron microscopy images (at 300.times. magnification) of abdominal white adipose and scapular adipose tissues. WAT, abdominal white adipose tissues; Scapula, scapular adipose tissues.

FIG. 3, comprising FIG. 3A indicates body weight change (kg). Rabbits were injected daily with recombinant GST or GST-Tat protein (1 mg) for 19 days, subcutaneously. The rabbits were fed ad libitum. The rabbits treated with GST-Tat weighed less from day 1 and weighed 500 g less at day 19. *P<0.05 versus GST control. n=4. Average of initial body weight of GST control and GST-Tat treated rabbit group is 1.98 kg and 2.02 kg, respectively. FIG. 3B indicates the average food intake during 19 days of treatment. The rabbits treated with GST-Tat ate 26.3% less food. *P<0.05 versus GST control. n=4. FIG. 3C indicates comparison of weight of abdominal fat and liver tissues. Fat and liver tissues were reduced by 40% and 24.2% respectively. *P<0.05 versus GST control. n=4.

FIG. 4, comprising FIG. 4A shows the effect of intraperitoneal (i.p.) injection of GST or GST-Tat on body weight in Lep−/− mice (n=5). GST-Tat (50-300 .mu.g) was i.p. injected daily between 5-6 p.m. Control mice were given the same dose of GST. Control and Tat groups were freely fed. Pair-fed animals were given the same amount of food as that consumed by Tat group on the previous day. *P<0.05 versus GST or pair-fed control. FIG. 4B indicates the average weights of ten mice tissues: heart, kidney, lung, liver, spleen, stomach, large intestine, small intestine, and abdominal fat tissue isolated from chronic GST or GST-Tat treatment. *P<0.001 versus control. FIG. 4C indicates the average daily food intake (g/day) during treatment of GST or GST-Tat in obese Lep−/− mice. *P<0.001 versus control. FIG. 4D shows physiological parameters related to total energy expenditure. Cold tolerance test at 4.degree. C. *P<0.02 versus control. FIG. 4E shows $O_2$ consumption ($VO_2$). *P<0.001 versus control. FIG. 4F indicates locomotor activity measured as an indicator of physical activity. *P<0.01 versus control.

FIG. 5, comprising (FIG. 5A) Male rabbits (n=4) were placed in a 4.degree. C. chamber and the rectal temperature was measured for 1 hr at 10 min intervals. *P<0.04 versus control. (FIG. 5B) Oxygen consumption ($VO_2$) was recorded every four minutes for 2 hrs using an $O_2$ analyser, after allowing the rabbits to adapt to the metabolic chamber for 1 hr. *P<0.001 versus control. The GST-Tat-treated animals showed 0.3.degree. C. higher body temperature, and the difference was further increased to 0.9.degree. C. at 30 min, suggesting an increased adoptive thermogenesis and increased energy expenditure in the cold room. In line with this data, the animals treated with GST-TatdMt consumed 20 to 30% more oxygen, indicating high metabolic rates. These two data suggest that GST-Tat-treated mice have high metabolic rates and burn more fat to generate more heat and energy. (FIG. 5C) Plasma glucose levels were measured before and at 10, 20, 30, 60, and 120 min after an IV injection of glucose (1.5 g/kg, 50% solution) in male rabbits (n=4) fasted for 16 hr. *P>0.9 versus control. (FIG. 5D) For ITT, the plasma glucose levels were measured before and at 5, 15, 30, 60, 90, and 120 min after an acute IV injection of human regular insulin (0.75 U/kg) in fed male rabbits. *P>0.15 versus control. The P-values suggest that there is no statistically significant difference in glucose homeostasis between the control and Tat-treated rabbits. (FIG. 5E) Glucose homeostasis is not altered by GST-Tat treatment of C57BL/6J Lep−/− mice. Glucose homeostasis tests. Plasma glucose levels were measured at various time points after an IP injection of glucose into fasted Lep−/− mice. *P>0.2 versus control. (FIG. 5F) For ITT, the plasma glucose levels were measured at various intervals after an IP injection of human regular insulin into fed Lep−/− mice. *P<0.02 versus control.

FIG. 6, comprising FIG. 6A shows the dorsal and ventral views of representative mice from the two test groups. The dorsal views of the inter-scapular adipose tissues are also shown. Intra-abdominal WAT (AbWAT) and the liver were compared. FIG. 6B shows histological and electron microscopic image comparison of the adipocytes and livers isolated from the control and GST-Tat-treated test group. AbWAT (1, 2), inter-scapular BAT (5, 6), and liver (11, 12) were fixed and stained with H&E. The tissues were analysed by Nikon light microscopy (200.times.; sub-figures 1, 2, 5, 6), SEM (300.times.; abWAT images 3, 4; BAT images 7, 8) and TEM (9800.times.; BAT images 9, 10). f, lipid; m, mitochondrion.

FIG. 7, comprising FIG. 7A shows the structure of the Tat expression construct. Tat expression is under the control of an ob gene promoter and SV40 enhancer. FIG. 7B shows the result of RT-PCR of Tat mRNA. Tat was expressed in the adipose tissues, liver, and muscle. W, white adipose tissue; B, brown adipose tissue; L, liver; M, muscle. FIG. 7C shows a ventral view of a transgenic mouse (Tg) and a control littermate (Wt) (1, 2). Tissue sections of intra-abdominal WAT, inter-scapular BAT, and muscle, all H&E stained (200.times.) (3-8). Ab, abdominal; WAT, white adipose tissue; BAT, brown adipose tissue.

FIG. 8, comprising FIG. 8A through FIG. 8F represents the physiological parameters related to total energy expenditure increase in FVB transgenic mice over-expressing Tat. Tg mice showed increases in the total energy expenditure in the form of physical activity and energy expenditure at the expense of fatty acid .beta.-oxidation.

FIG. 9, comprising

FIG. 10, comprising FIG. 10A shows diagram of full length Tat (101 amino acids) and Tat fragments (filled black bars) tested for fat reduction in rabbit. Tat (72 amino acids) is transcriptionally competent. PTD, protein transduction domain. Tat fragment (a.a. 24-57) were tested for anorexic effect but not included in the test in rabbit. FIG. 10B shows SDS-PAGE gel of purified recombinant GST, and GST-Tat fragment proteins. M, molecular size marker. FIG. 10C indicates the results for comparison of fat mass of abdominal, scapular and heart fat in rabbits treated with various recombinant Tat polypeptides. Rabbits were injected 4 times with two week intervals with recombinant GST or GST-Tat fragments (1 mg), subcutaneously. The rabbits were fed ad libitum. 10 days after final injection tissues were collected and pictured.

FIG. 11, comprising FIG. 11A shows the result of RT-PCR analysis of expression changes of the mRNA involved in the lipid catabolism and energy expenditure in FVB transgenic mice expressing Tat. FIG. 11B shows the result of Western blot analysis of eNOS using 30 .mu.g of tissue extracts. .beta.-actin serves as a control. A higher level of eNOS protein was detected in WAT, BAT and muscle. FIG. 11C shows that plasma NO concentration measured by nitrate/nitrite assay was increased by 20% in Tg mice, compared to the control littermates. .alpha.-actin serves as a control. .beta.-AR, adrenergic receptor; BAT, brown adipose tissue; HSL, hormone-sensitive lipase; PGC-1.alpha., peroxisomal proliferative gamma cofactor-1; UCP1, uncoupling protein-1; WAT, white adipose tissue; Tg, FVB transgenic mice overexpressing Tat; Con, control littermates.

DETAILED DESCRIPTION

In one aspect of this invention, there is provided a composition for preventing, alleviating or treating obesity comprising a peptide having the amino acid sequence of SEQ ID NO:1 or NO:2.

The present inventors have made intensive studies to develop a novel composition for preventing, alleviating or treating obesity. As results, the present inventors have discovered that partial fragments of Tat has a potent fat reducing effect by significantly reducing food-intake by activation of the central melanocortin system, and also by increasing total energy expenditure in mice and rabbits.

The term "peptide" as used herein, refers to a linear molecule formed by peptide bonds between amino acid residues.

The peptide of the present invention is a partial fragment of Tat (Trans activator of transcription), a major regulatory protein of HIV-1. Administration of Tat fragment caused severe weight loss by reducing fat mass of BAT, WAT, and liver of mice and rabbits.

Another effect of the peptide of this invention on energy metabolism is anorexia. Central and peripheral administration of Tat fragment reduced food-intake, indicating that that reduction in food intake is one of the major contributors to Tat-induced weight loss. A lower dose (1/100 to 1/1000 of the dose of i.p. administration, 0.01-0.1 nmol) of Tat fragment caused severe anorexia when administered by i.c.v. Thus, Tat caused a decrease in food-intake by acting at the central nervous system.

SEQ ID NO:1 and NO:2 represent the shorter, middle fragments of Tat, Tat (a.a. 20-45) and Tat (a.a. 20-57), respectively. According to the present invention, Tat (a.a. 20-45) and Tat (a.a. 20-57) show excellent efficacy in reducing food-intake and weight. In contrast, C- and N-terminal fragments, Tat (a.a. 1-25) and Tat (a.a. 40-72) had no effect on body weight and food intake.

Accordingly, the present invention achieves superior effect, easier synthesis and lower risk of side effect compared to the full length of Tat through using partial fragment only involved in the function of interest.

According to a preferred embodiment, the peptide of this invention has the amino acid sequence of SEQ ID NO:2.

Figure 9A:
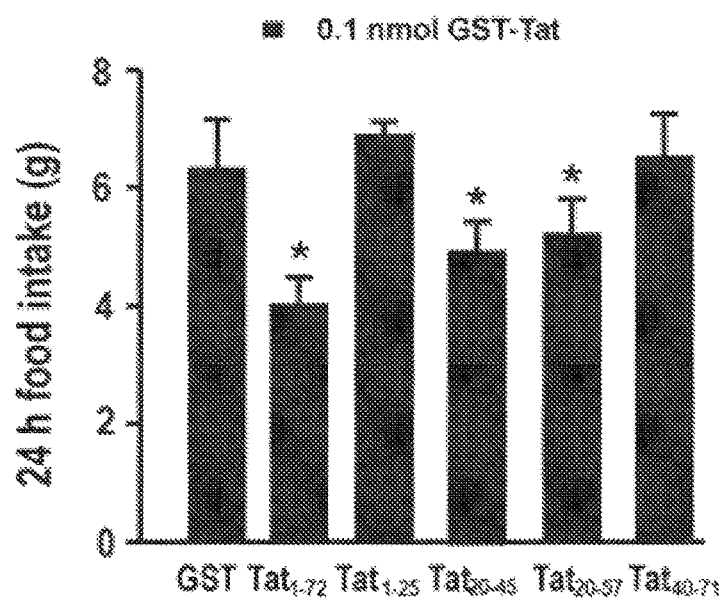
FIG. 9A and FIG. 9B, represents that central administration of Tat decreases body weight and food-intake. Changes in body weight (FIG. 9B) and food intake (FIG. 9A) during 24 hrs following i.c.v. administration of GST or GST-Tat polypeptides (0.1 nmol) are shown. Mice were fasted overnight before study. n=7 per group. * P<0.05 vs. GST-injected control.
Figure 9B:
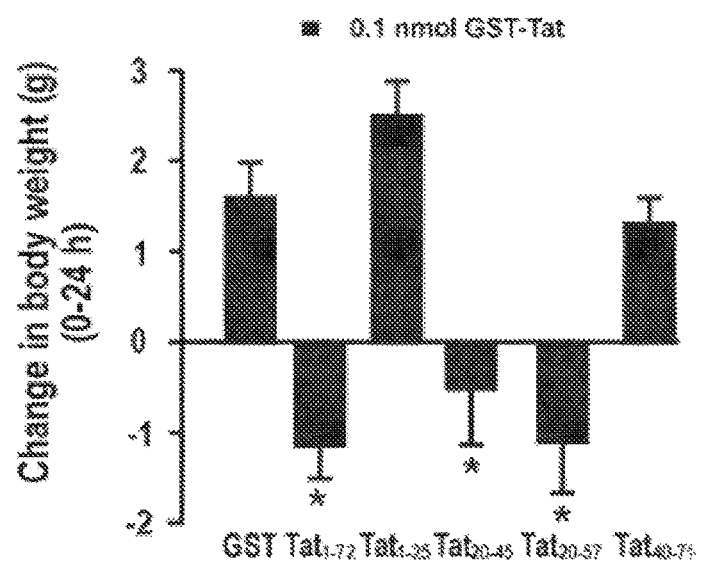

SEQ ID NO:2 represents the fragment of Tat (a.a. 20-45). As shown in Examples below, administration of this fragment exhibits most severe weight loss (FIG. 9).

In another aspect of this invention, there is provided a composition for preventing, alleviating or treating obesity comprising a nucleotide encoding the amino acid sequence of SEQ ID NO:1 or NO:2.

It would be obvious to the skilled artisan that the nucleotide sequences used in this invention are not limited to those listed in the appended Sequence Listings.

For nucleotides, the variations may be purely genetic, i.e., ones that do not result in changes in the protein product. This includes nucleic acids that contain functionally equivalent codons, or codons that encode the same amino acid, such as six codons for arginine or serine, or codons that encode biologically equivalent amino acids.

Considering biologically equivalent variations described hereinabove, the nucleic acid molecule of this invention may encompass sequences having substantial identity to them. Sequences having the substantial identity show at least 60%, preferably at least 70%, more preferably at least 80%, most preferably at least 90% similarity to the nucleic acid molecule of this invention, as measured using one of the sequence comparison algorithms. Methods of alignment of sequences for comparison are well-known in the art. Various programs and alignment algorithms are described in: Smith and Waterman, *Adv. Appl. Math.* 2:482 (1981); Needleman and Wunsch, *J. Mol. Bio.* 48:443 (1970); Pearson and Lipman, *Methods in Mol. Biol.* 24: 307-31 (1988); Higgins and Sharp, *Gene* 73:237-44 (1988); Higgins and Sharp, CABIOS 5:151-3 (1989) Corpet et al., *Nuc. Acids Res.* 16:10881-90 (1988) Huang et al., *Comp. Appl. BioSci.* 8:155-65 (1992) and Pearson et al., *Meth. Mol. Biol.* 24:307-31 (1994). The NCBI Basic Local Alignment Search Tool (BLAST) [Altschul et al., *J. Mol. Biol.* 215:403-10 (1990)] is available from several sources, including the National Center for Biological Information (NBCI, Bethesda, Md.) and on the Internet, for use in connection with the sequence analysis programs blastp, blasm, blastx, tblastn and tblastx. It can be accessed at http://www.ncbi.nlm.nih.gov/BLAST/. A description of how to determine sequence identity using this program is available at http://www.ncbi.nlm.nih.gov/BLAST/blast_help.html.

According to a preferred embodiment, the nucleotide of this invention encodes the amino acid sequence of SEQ ID NO:2.

According to a preferred embodiment, the nucleotide encoding the amino acid sequence of SEQ ID NO:1 has the nucleotide sequence of SEQ ID NO:3.

According to a preferred embodiment, the nucleotide encoding the amino acid sequence of SEQ ID NO:2 has the nucleotide sequence of SEQ ID NO:4.

According to a preferred embodiment, the composition of this invention is selected from the group consisting of pharmaceutical composition, functional food composition and cosmeceutical composition.

The composition of this invention may be provided as a pharmaceutical composition comprising a pharmaceutically effective amount of the peptide or the nucleotide of this invention.

The term "pharmaceutically effective amount" as used herein, refers to an amount enough to show and accomplish efficacies and activities for preventing, alleviating, or treating obesity.

The pharmaceutical composition of this invention includes a pharmaceutically acceptable carrier besides the active ingredient compound. The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995).

The pharmaceutical composition according to the present invention may be administered orally or parenterally, and preferably, administered parenterally. For parenteral administration, it may be administered intravenously, subcutaneously, intramuscularly, intraperitoneally, topically transdermally.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, pharmaceutical composition of the present invention may be administered with a daily dosage of 0.001-100 mg/kg (body weight).

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include a solution, a suspension or an emulsion in oil or aqueous medium, an elixir, a powder, a granule, a tablet and a capsule, and may further comprise a dispersion agent or a stabilizer.

The composition of this invention may be provided as a cosmeceutical composition comprising a cosmeceutically effective amount of the peptide or the nucleotide of this invention.

The term "cosmeceutically effective amount" as used herein, refers to an amount enough to show and accomplish efficacies and activities for preventing, alleviating, or treating obesity.

The cosmeceutical compositions of this invention may be formulated in a wide variety of form, for non-limited example, including a solution, a suspension, an emulsion, a paste, a gel, a cream, a lotion, a powder, a soap, a surfactant-containing cleanser, an oil, a powder foundation, an emulsion foundation, a wax foundation and a spray. In detail, the cosmeceutical composition of the present invention can be provided in a form of skin softener (skin lotion), nutrient emulsion, nutrient cream, message cream, essence, eye cream, cleansing cream, cleansing foam, cleansing water, facial pack, spray or powder.

The cosmeceutically acceptable carrier contained in the present cosmeceutical composition, may be varied depending on the type of the formulation. For example, the formulation of pastes, creams or gels may comprise animal and vegetable fats, waxes, paraffins, starch, tragacanth, cellulose derivatives, polyethylene glycols, silicones, bentonites, silica, talc, zinc oxide or mixtures of these ingredients.

In the formulation of powder or spray, it may comprise lactose, talc, silica, aluminum hydroxide, calcium silicate, polyamide powder or mixtures of these ingredients. Spray may additionally comprise the customary propellants, for example, chlorofluorohydrocarbons, propane/butane or dimethyl ether.

The formulation of solution and emulsion may comprise solvent, solubilizer or emulsifier, for example water, ethanol, isopropanol, ethyl carbonate, ethyl acetate, benzyl alcohol, benzyl benzoate, propylene glycol, 1,3-butyleneglycol oils, glycerol fatty esters, polyethylene glycol, fatty acid esters of sorbitan or mixtures of these ingredients.

The formulation of suspension may comprise liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these ingredients.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

The cosmeceutical compositions of the present invention may contain auxiliaries as well as carrier in addition to the peptide or the nucleotide of the present invention as active ingredients. The non-limiting examples of auxiliaries include antioxidants, stabilizers, solubilizers, vitamins, colorants, odor improvers or mixtures of these ingredients.

The composition of this invention may be prepared as a functional food composition. The food composition of this invention may comprise conventional additives for preparing food compositions, e.g., protein, carbohydrates, lipids, nutritive substances and flavors.

Examples of carbohydrates described above include, but not limited to, monosaccharide (e.g., glucose and fructose); disaccharide (e.g., maltose, sucrose and oligosaccharide); and polysaccharide (e.g., dextrin and cyclodextrin); and sugar alcohol (e.g., xylitol, sorbitol and erythritol). Non-limiting examples of Flavors include, but not limited to, natural flavors [thaumatin and extract of stevia (e.g., rebaudioside A and glycyrrhizin)] and synthetic flavors (e.g., saccharin and aspartame).

Considering higher accessibility to food, the composition of the present invention may be effectively used for functional food for preventing, alleviating or treating obesity.

According to a preferred embodiment, the peptide of this invention inhibits generation of adipose tissue or promotes reduction of adipose tissue.

The present inventors have discovered that Tat fragment peptides of this invention contribute to reduction of fat via multiple mechanisms. According to the present invention, Tat-treated rabbits, obese Lep−/− mice, and transgenic FVB mice all showed increased body temperature and increased thermogenesis in response to cold. Also, the animals showed a marked increase in locomotor activity. Hormone-sensitive lipase (HSL), which is a key regulator of lipid metabolism; and PGC-1α (PPAR gamma coactivator 1 alpha), Cyt-C (cytochrome c), COXII (cytochrome c oxygenase subtype II), and UCPs (uncoupling proteins), which are critical in mitochondrial biogenesis, function, and thermogenesis, were also expressed at higher levels. These alterations in gene expression and animal physiological data suggested that Tat fragments increase lipolysis, β-oxidation of free fatty acids, thermogenesis, and total energy expenditure.

a. According to a preferred embodiment, the peptide of this invention induces anorexia.
b. Administration of Tat fragment causes reduction in food intake, which is one of the major contributors to Tat-induced weight loss. Tat fragment caused severe anorexia when administered by i.c.v. demonstrating that Tat fragment caused a decrease in food-intake by acting at the central nervous system.
c. According to a preferred embodiment, the nucleotide of this invention is contained in a gene delivery system.
d. The term "gene delivery system" as used herein, refers to any forms of carriers that harbor and transport exogenous nucleic acid molecules to a target cell or tissue. The ideal gene delivery system should be harmless to human body, suitable for mass production, and capable of effective transportation of the target gene.
e. The term "gene delivery" used herein refers to the transfer of gene into cells and has the same meaning as gene transduction. In tissue level, the gene delivery becomes the same meaning as spread of gene. Therefore, the gene delivery system of this invention is also expressed as either gene transduction system or gene spreading system.
f. To construct the present gene delivery system of this invention, it is preferred that the nucleotide sequence of this invention is contained in a suitable expression construct. According the expression construct, it is preferred that the nucleotide sequence of this invention is operably linked to a promoter. The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.
g. According to the present invention, the promoter linked to the nucleotide sequence of this invention is operable in, preferably, animal, more preferably, mammalian cells, to control transcription of the nucleotide sequence of this invention, including the promoters derived from the genome of mammalian cells or from mammalian viruses, for example, CMV (cytomegalovirus) promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter and human GM-CSF gene promoter. Most preferably, the promoter is CMV promoter.
h. Preferably, the expression construct used in this invention comprises a polyadenylation sequence (e.g., bovine growth hormone terminator and SV40-derived polyadenylation sequence).
i. The gene delivery system of the present invention is constructed in a variety of forms, preferably, (i) naked recombinant DNA molecule, (ii) plasmid, (iii) viral vector, or (iv) liposome or niosome containing naked recombinant DNA molecule and plasmid.
j. The nucleotide sequence of this invention may be applied to a multitude of gene delivery systems useful in gene therapy, preferably, plasmid, adenovirus (Lockett U, et al., Clin. Cancer Res. 3:2075-2080 (1997)), adeno-associated virus (AAV, Lashford L S., et al., Gene Therapy Technologies, Applications and Regulations Ed. A. Meager, 1999), retrovirus (Gunzberg W H, et al., Retroviral vectors. Gene Therapy Technologies, Applications and Regulations Ed. A. Meager, 1999), lentivirus (Wang G. et al., J. Clin. Invest. 104(11):R55-62 (1999)), herpes simplex virus (Chamber R., et al., Proc. Natl. Acad. Sci USA 92:1411-1415 (1995)), vaccinia virus (Puhlmann M. et al., Human Gene Therapy 10:649-657 (1999)), liposome (Methods in Molecular Biology, Vol 199, S. C. Basu and M. Basu (Eds.), Human Press 2002) or niosome. Most preferably, the gene delivery system of this invention is constructed by incorporating the nucleotide of this invention to a plasmid.
k. Where the present gene delivery system is constructed on the basis of viral vector construction, the contacting is performed as conventional infection methods known in the art. The infection of hosts using viral vectors is well described in the above-cited publications.
l. Where the present gene delivery system is a naked recombinant DNA molecule or plasmid, the Nkx3.2-encoding sequence to be delivered are introduced into cells by microinjection (Capecchi, M. R., Cell, 22:479 (1980) and Harland and Weintraub, J. Cell Biol. 101: 1094-1099 (1985)), calcium phosphate co-precipitation (Graham, F. L. et al., Virology, 52:456 (1973) and Chen and Okayama, Mol. Cell. Biol. 7:2745-2752 (1987)), electroporation (Neumann, E. et al., EMBO J., 1:841 (1982) and Tur-Kaspa et al., Mol. Cell Biol., 6:716-718 (1986)), liposome-mediated transfection (Wong, T. K. et al., Gene, 10:87 (1980) and Nicolau and Sene, Biochim. Biophys. Acta, 721:185-190 (1982); and Nicolau et al., Methods Enzymol., 149:157-176 (1987)), DEAE-dextran treatment (Gopal, Mol. Cell Biol., 5:1188-1190 (1985)), and particle bombardment (Yang et al., Proc. Natl. Acad. Sci., 87:9568-9572 (1990)).

EXAMPLES

Materials And Methods

1. Animal Experiments

Obese male mice (C57BL/6J Lep−/−, nine weeks old, n=6) were purchased from Jackson Laboratories. All of the animal procedures were performed in accordance with the guidelines of the Institutional Animal Care and Use Committee of Yonsei University. The mice were injected daily with 300-50 μg of the recombinant GST-Tat or GST, and were fed a standard chow diet ad libitum for 2 weeks. Body weight and food intake were recorded daily. Male white rabbits (n=4), weighing 1.5-1.8 kg, were injected subcutaneously with 1 mg of either GST-Tat or GST four times at two-week intervals, and their body weights were recorded daily. The rabbits were fed a regular chow diet.

2. Oxygen Consumption, Cold Tolerance and Locomotor Activity $O_2$ consumption ($VO_2$) and $CO_2$ production ($VCO_2$) of the mice and rabbits were measured using an Oxymax apparatus (Columbus Instruments, Columbus, Ohio). The $VO_2$ is expressed as the volume of $O_2$ consumed per g or kg of body weight per minute for mice and rabbits, respectively. Based on the $VO_2$ and $VCO_2$, the heat dissipated was calculated according to the formula provided by the manufacturer: Energy expenditure=[3.815+1.232($VCO_2NO_2$)]× $VO_2$. Adaptive thermogenesis was monitored by measuring the rectal temperature under 4° C. cold stress. An activity monitor (MED Associates Inc., St. Albans, Vt.) was used to measure the ambulatory counts.

3. Measurement of Fatty Acid Oxidation

The mouse tissues, including those of the WAT, BAT, liver and muscle, were collected from the transgenic mice. The level of [1-$^{14}$C]-palmitate (NEN DuPont, Wilmington, Del.) oxidation was analyzed in the tissue extracts by measuring the [14C]-CO2 trapped in Solvable (Packard Bioscience, Meriden, Conn.).

4. Recombinant Tat Polypeptides

The recombinant Tat polypeptide was prepared by cloning Tat cDNA fragments (72, 1-25, 20-45, 24-57, 40-71 a.a.) into pGex4T3 (Pharmacia, Piscataway, N.J.) and by its overexpression in *E. coli* BL21 (DE3). Recombinant GST and GST-Tat were purified by affinity chromatography using Glutathione Agarose 4B (Sigma, St. Louis, Mo.).

5. Total RNA Analysis and Western Blot Analysis

Total RNA (10 μg) was prepared using TRIzol Reagent (Invitrogen, Carlsbad, Calif.), and analyzed using the standard Northern protocol. For RT-PCR, the total RNA (10 μg) was reverse-transcribed using SuperScript™ II Reverse Transcriptase (Invitrogen). The oligonucleotide primers used in RT-PCR for β-AR 1, 2, 3, AC7, HSL, VEGF-D, PGC-1α, UCP1, 2, 3, and COXII are listed in Table 1. Western blotting of the various tissue homogenates was carried out using antibodies against β-actin (Santa Cruz Biotechnology, Santa Cruz, Calif.) and eNOS (BD Biosciences, Palo Alto, Calif.).

TABLE 1

The oligonucleotide primers used in RT-PCR of the mRNAs involved in lipid catabolism and energy expenditure.

| Gene name | Primer sequence (forward and reverse) |
|---|---|
| β-AR 1 | Forward primer 5'-GATCGAATTCAACCATGGGCGCGGGGGCGCTCGCCCTG-3' (SEQ ID NO: 5)<br>Reverse primer 5'-GATCCTCGAGCTGGTAGCGAAAGGGCGACGTGATG-3' (SEQ ID NO: 6) |
| β-AR 2 | Forward primer 5'-GATCGAATTCAACCATGGGGCCACACGGGAACGACAGC-3' (SEQ ID NO: 7)<br>Reverse primer 5'-GATCCTCGAGCAAAAAGGAGGTAAGGCCAGATACA-3' (SEQ ID NO: 8) |
| β-AR 3 | Forward primer 5'-GATCGAATTCAACCATGGCTCCGTGGCCTCACAGAAAC-3' (SEQ ID NO: 9)<br>Reverse primer 5'-GATCCTCGAGAAAGGACACGGCAGCGGACACGATC-3' (SEQ ID NO: 10) |
| AC7 | Forward primer 5'-GCCAAGGGGCGCTACTTCCTAAAT-3' (SEQ ID NO: 11)<br>Reverse primer 5'-AAGGCTCTTGTCACAGCTCCAAAC-3' (SEQ ID NO: 12) |
| HSL | Forward primer 5'-GATCGAATTCAACCATGGATTTACGCACGATGACACAG-3' (SEQ ID NO: 13)<br>Reverse primer 5'-GATCCTCGAGGCGGCCGTAGAAGCAGCCTTTGTGT-3' (SEQ ID NO: 14) |
| VEGF-D | Forward primer 5'-ATGTGTGGAGAATGGGGAATGGGG-3' (SEQ ID NO: 15)<br>Reverse primer 5'-GAGATGTAGGAGGTGCTTGTGTTC-3' (SEQ ID NO: 16) |
| PGC-1α | Forward primer 5'-GATCGAATTCAACCATGGCTTGGGACATGTGCAGCCAA-3' (SEQ ID NO: 17)<br>Reverse primer 5'-GATCCTCGAGATGGTTCTGAGTGCTAAGACCGCTG-3' (SEQ ID NO: 18) |
| UCP 1 | Forward primer 5'-GATCGAATTCAACCATGGTGAACCCGACAACTTCCG-3' (SEQ ID NO: 19)<br>Reverse primer 5'-GATCCTCGAGTTATGTGGTACAATCCACTGTCTG-3' (SEQ ID NO: 20) |

TABLE 1-continued

The oligonucleotide primers used in RT-PCR of the mRNAs involved in lipid catabolism and energy expenditure.

| Gene name | Primer sequence (forward and reverse) |
|---|---|
| UCP 2 | Forward primer 5'-GATCGAATTCAACCATGGTTGGTTTCAAGGCCACAG-3' (SEQ ID NO: 21)<br>Reverse primer 5'-GATCCTCGAGTCAGAAAGGTGCCTCCCGAGATTG-3' (SEQ ID NO: 22) |
| UCP 3 | Forward primer 5'-GATCGAATTCAACCATGGTTGGACTTCAGCCCTCCGAAG-3' (SEQ ID NO: 23)<br>Reverse primer 5'-GATCCTCGAGTCAAAACGGAGATTCCCGCAGTACC-3' (SEQ ID NO: 24) |
| COXII | Forward primer 5'-GATCGAATTCACCATGGCCTACCCATTCCAACTTGGT-3' (SEQ ID NO: 25)<br>Reverse primer 5'-GATCCTCGAGTTAAATTATTGAAGCAGATCAGTT-3' (SEQ ID NO: 26) |

6. Tissue Collection and Histology

The tissues from the Lep−/− (23-week-old) and transgenic (24-week-old) mice were collected, fixed, embedded in paraffin, and sliced. The tissue sections were stained with hematoxylin and eosin (H&E).

7. Electron Microscopy

Tissue pieces for SEM were fixed and dehydrated using standard protocols. The samples were dried, gold coated to a thickness of 300 Å, and examined through a Hitachi S-800 scanning electron microscope. Tissue pieces for TEM were fixed, dehydrated, embedded, and sliced into ultra thin sections using standard methods. The tissue sections were examined with a Philips CM-10 transmission electron microscope.

8. Tat-Overexpressing Transgenic Mice

The cDNA-encoding Tat (72 a.a.) was cloned into an expression vector, a pcDNA3.0 derivative containing an SV40 enhancer, murine ob promoter, ob signal peptide, and a 6×His tag (2). Three FVB transgenic founder lines were obtained. Genotyping was performed using PCR and Southern blotting. Fat mass of transgenic mice was measured using PIXImus™ mouse densitometer (GE healthcare, USA).

9. Microarray Analysis with Affymetrix Gene Chips

Total RNA was isolated from the control and Tat-treated mice by TRIzol (Invitrogen, Carlsbad, Calif.) and cleaned using an RNeasy Mini Kit (Qiagen, Valencia, Calif.). The RNA (10 µg) was reverse transcribed with the T7 $(dT)_{24}$ primer. The double-stranded cDNA was transcribed in vitro with T7 RNA polymerase and biotin-labeled ribonucleotides (Affymetrix, Santa Clara, Calif.). The biotin-labeled cRNA was fragmented at 94° C. for 35 min. The cRNA (15 µg) was hybridized onto a high density Affymetrix GeneChip (Mouse Genome 430, 2.0) at the SeouLin Bioscience GeneChip service, which is the Korean representative of Affymetrix (Seoul, Korea). GeneChip data analysis was performed with GeneChip Operation Software (GCOS) and Data Mining Tool (DMT) software according to the Affymetrix GeneChip Analysis Manual (Affymetrix Inc.).

10. Glucose Tolerance and Insulin Tolerance Tests (GTT, ITT)

The GTT was performed on 23-week-old Tat-treated Lep−/− mice (n=6) and rabbits (n=4). D-glucose (1.5 g/kg body weight) (Sigma, St. Louis, Mo.) was injected either intraperitoneally or intravenously into animals that had fasted for 16 hrs. For the ITT, the animals were injected with 0.75 U/kg body weight of human insulin (Eli Lilly & Co., Indianapolis, Ind.). Serum glucose was measured using SureStep (LifeScan, Milpitas, Calif.).

11. I.C.V. Cannulation and Injection.

26 gauge cannulae were implanted into the 3rd ventricle (1.8 mm caudal to the bregma and 5.0 mm ventral to the sagittal sinus) of C57BL/6J mice as previously described. Following a 7-day recovery period, the animals were handled every day for 1 week to minimize stress. Correct position of the cannula was confirmed by a positive dipsogenic response to angiotensin II (50 ng). GST, GST-Tat or GST-Tat fragment was dissolved in 0.9% saline and administered i.c.v. in a volume of 2 µl over 1 min following overnight fast. Tat or Tat fragment was administered ICV 1 h prior to IP or i.c.v. Tat injection.

12. Statistical Analysis.

Data are reported as the mean±SEM. The significant differences were determined by Student's t-test (*). In the case of three group experiments, Kruskal-Wallis test was used.

Results

Chronic Administration of Tat Decreased Fat Mass in Obese Lep−/− Mouse and Rabbit.

Figure 1A:
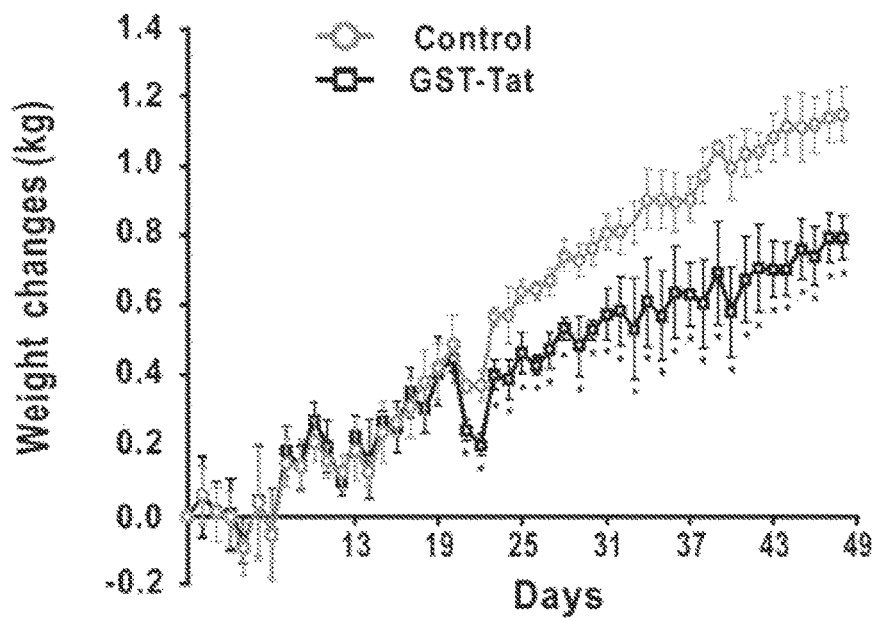
FIG. 1A and FIG. 1B, represents that Tat reduces fat mass in rabbits.
Figure 1B:
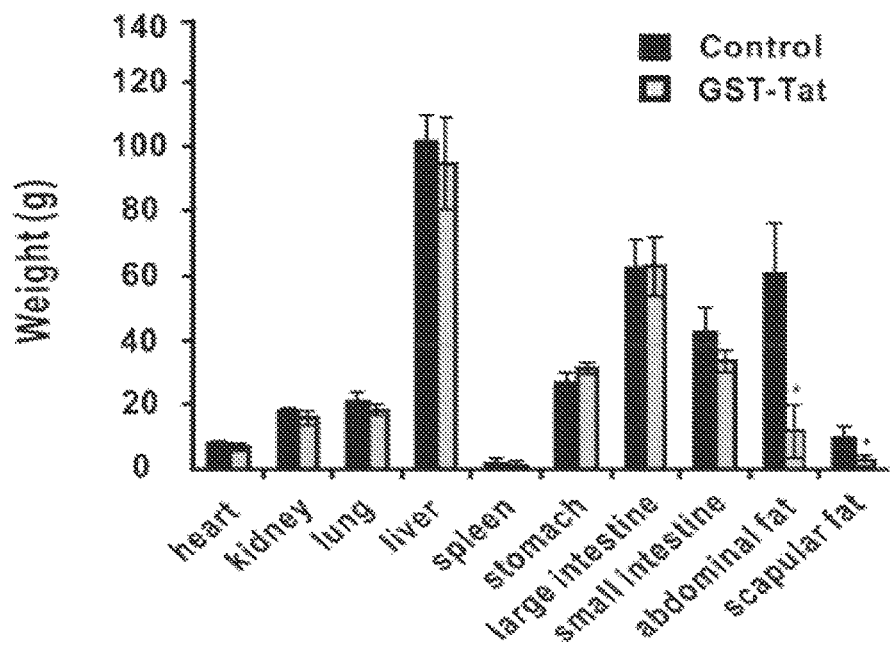
Figure 2A:
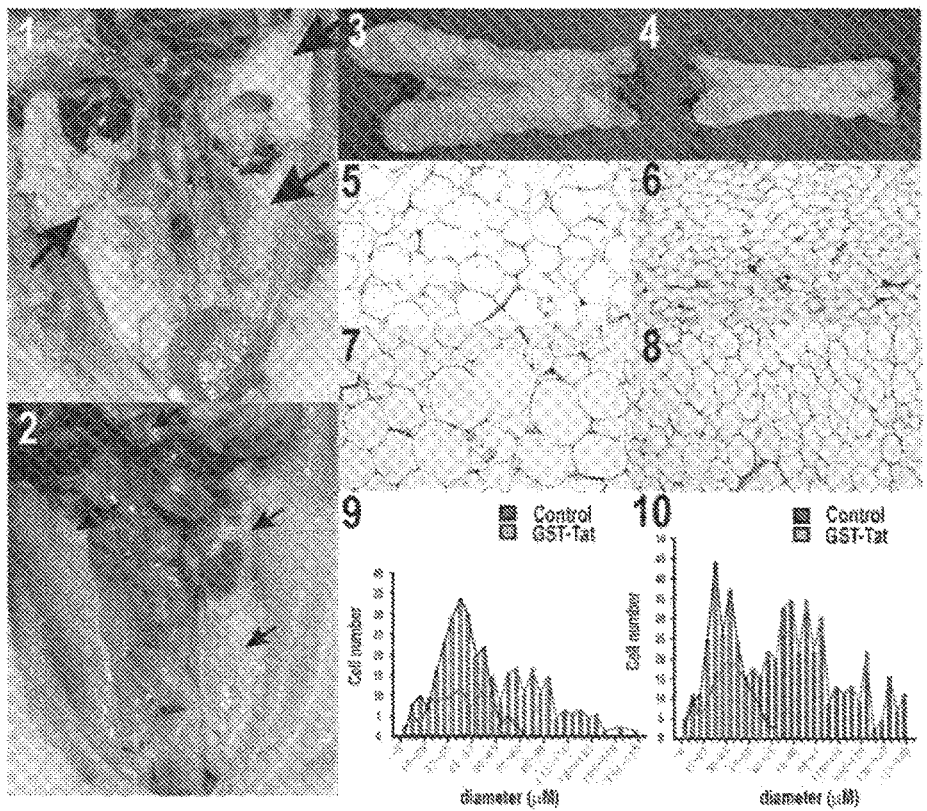
FIG. 2A and FIG. 2B, represents that Tat reduces the size of abdominal and scapular adipocytes in rabbits.
Figure 2B:
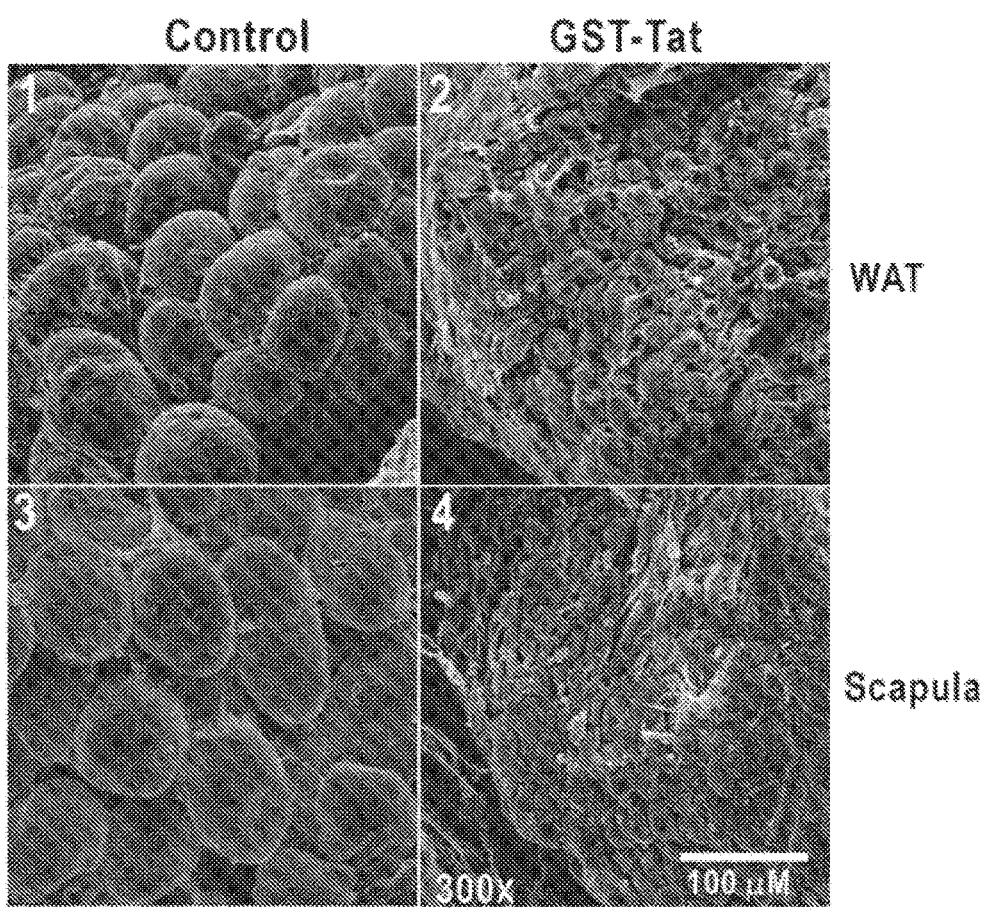

To test the effect of Tat on body weight, control vehicle or recombinant GST-Tat (1 mg) was injected subcutaneously into white rabbits four times at two-week intervals. Chronic administration of GST-Tat induced a significant weight loss after three weeks of the injection. At seven weeks, the rabbits treated with GST-Tat weighed 380 g less compared to the controls treated with GST (FIG. 1a). When changes in tissue weight were analysed, intra-abdominal and scapular fat mass was significantly reduced, while other organ weights remained unchanged (FIG. 1b). This data suggested that Tat-induced weight loss was largely due to a reduction in fat mass. Histological and scanning electron microscopic examination revealed that average fat cell size was reduced in abdominal adipose tissue of Tat-treated rabbits (average diameter: Tat 75-80 µm vs. control 40 µm) (FIGS. 2a and 2b).

Figure 3A:
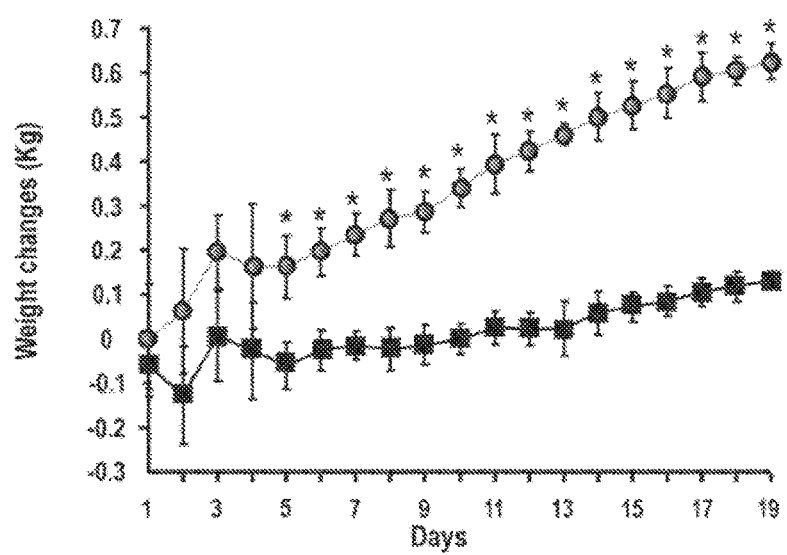
FIG. 3A through FIG. 3C, represents that Tat reduces body weight in rabbits.
Figure 3B:
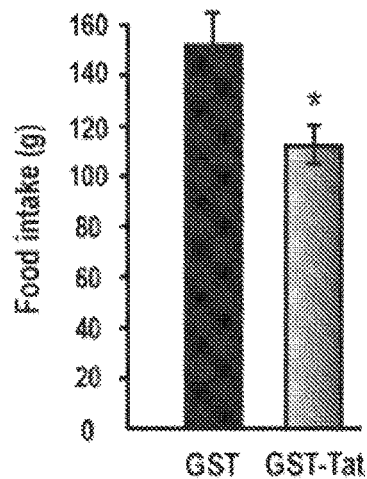
Figure 3C:
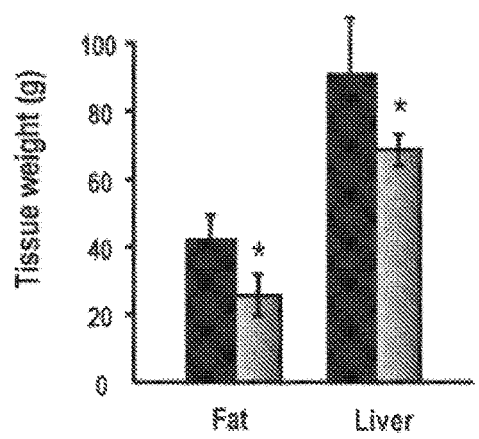

Because rabbits showed marked weight loss only after two weeks of initial Tat treatment in the above experiment, the present inventors injected rabbits with GST or recombinant GST-Tat (1 mg) daily for 20 days. Daily injection of GST-Tat induced a strong anorexic effect and weight reduction starting at day one (FIG. 3a). At 20 days, the rabbits treated with GST-Tat weighted 500 g less compared to the controls treated with GST and GST-Tat rabbits ate 40 g less than controls under ad libitum condition (FIG. 3b). The tissue weight of abdominal fat and liver was decreased by 40% and 24.2% respectively (FIG. 3c).

Figure 4A:
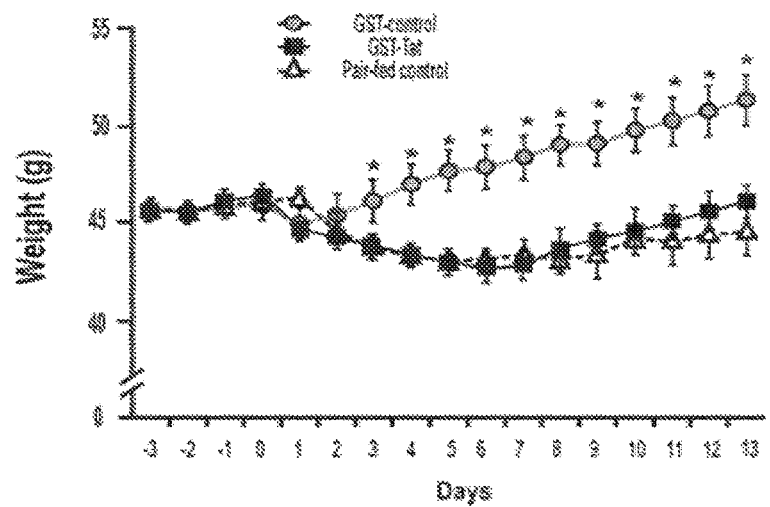
FIG. 4A through FIG. 4F, represents that Tat reduces the fat mass in C57BL/6J Lep−/− mice.
Figure 4B:
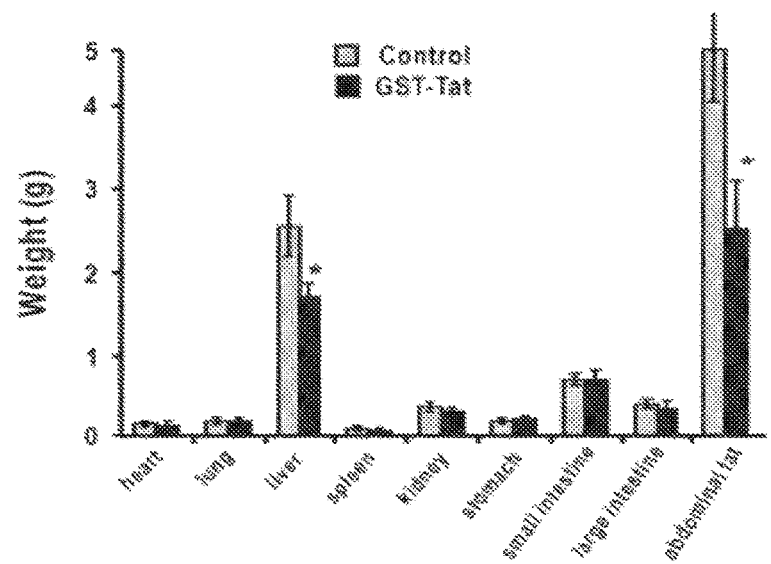
Figure 4C:
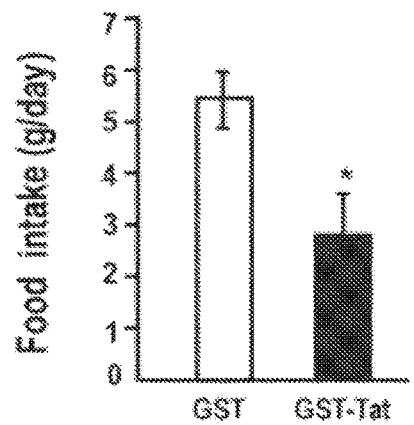

To examine whether Tat fragment can reduce fat mass in other species of animals, the present inventors administered GST-Tat (50-300 µg) intraperitoneally into obese Lep-/- mice for 2 weeks. Similarly to rabbits, chronic administration of GST-Tat decreased body weight by 3.59 g (FIG. 4a). The tissue weight of intra-abdominal fat and liver isolated from the obese Lep-/- mice treated with GST-Tat for 50 days was decreased by 49% (2.3 g) and 33.9% (0.91 g), respectively, while other tissues remain unchanged (FIG. 4b). To identify the mechanism by which Tat causes reduced fat mass, the present inventors measured food intake during Tat treatment in Lep-/- mice. Interestingly, the Tat treated Lep-/- mice consumed 49% (2.68 g) less food than the control, suggesting that Tat has significant effect on food intake (FIG. 4c).

Tat Polypeptide Treatment Increased Energy Expenditure by Increasing Thermogenesis and Oxygen Consumption.

Figure 4D:
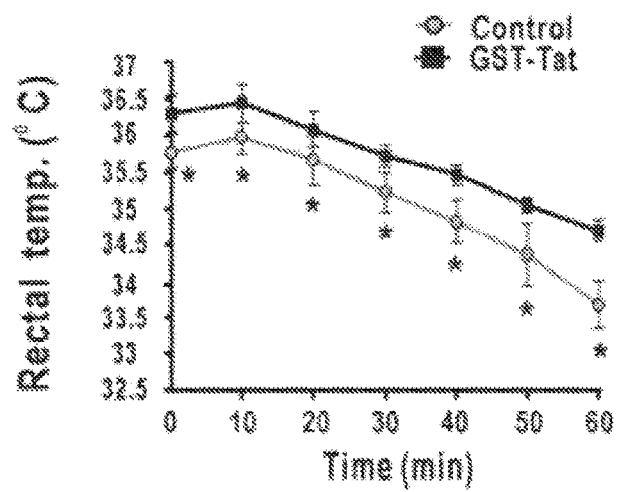
Figure 4E:
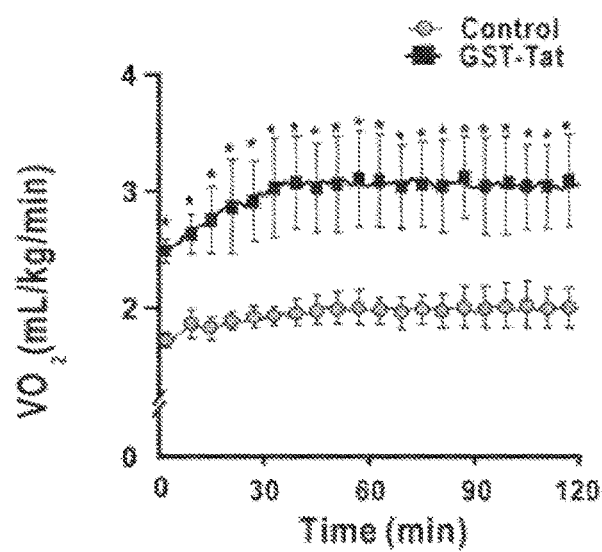
Figure 4F:
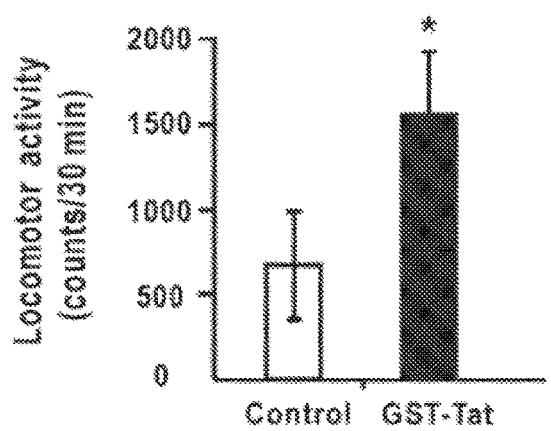
Figure 5A:
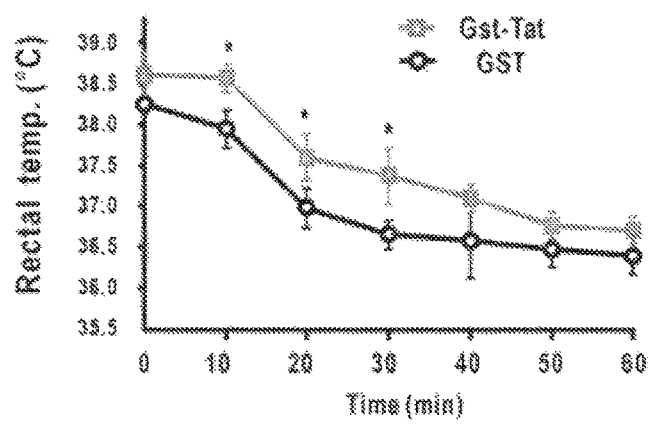
FIG. 5A through FIG. 5F, represents that Tat increases thermogenesis and oxygen consumption, but does not alter glucose homeostasis in rabbits.
Figure 5B:
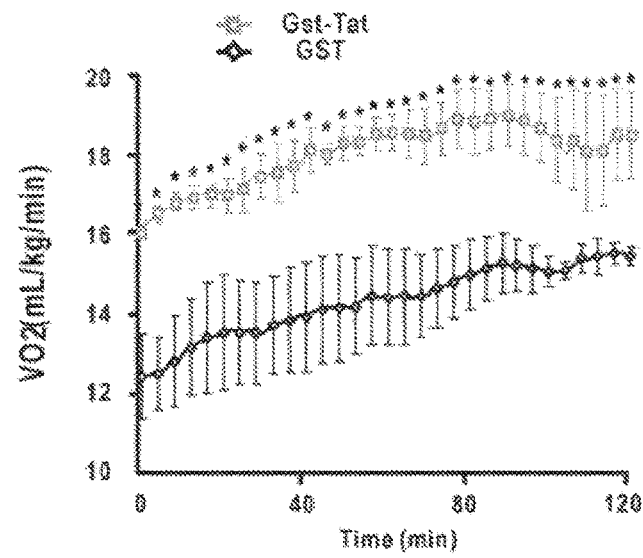

Although decreased food intake is one of the key factors in weight loss, other factors such as increased total energy expenditure and metabolic rate can also contribute to weight reduction because energy expenditure is a significant component of the energy balance and regulation of fat mass. Therefore, Tat-treated Lep-/- mice were further examined to determine if there was an increase in energy dissipation. The Tat-treated Lep-/- mice showed a body temperature that was 0.52° C. higher than the control mice under normal conditions. This difference increased by 1.02° C. within 60 min after the mice were placed in a 4° C. chamber, suggesting that Tat caused an increase in thermogenesis (FIG. 4d). Oxygen consumption by the animals was analysed for two hours, following a one-hour adaptation period. The Tat-treated Lep-/- mice consumed 54% more oxygen than the controls, and their average rate of consumption was 1.1 mL/g/min (FIG. 4E). Increased physical activity can also partially account for increased energy expenditure. Therefore, the mice were further examined, and it was found that the Tat-treated mice showed a two-fold increase in locomotor activities relative to the controls (FIG. 4f). The present inventors observed similar changes in metabolic papameteres in the rabbits treated with Tat (FIGS. 5a and 5b). The decrease in fat mass and the increase in energy expenditure in the form of physical activity and heat dissipation in the Tat-treated Lep-/- mice and rabbits suggests that Tat may cause the animals to burn more fat to meet a high total energy expenditure.

Insulin Sensitivity and Glucose Adsorption Remain Unchanged After Significant Weight Loss Following Tat Treatment.

Figure 5C:
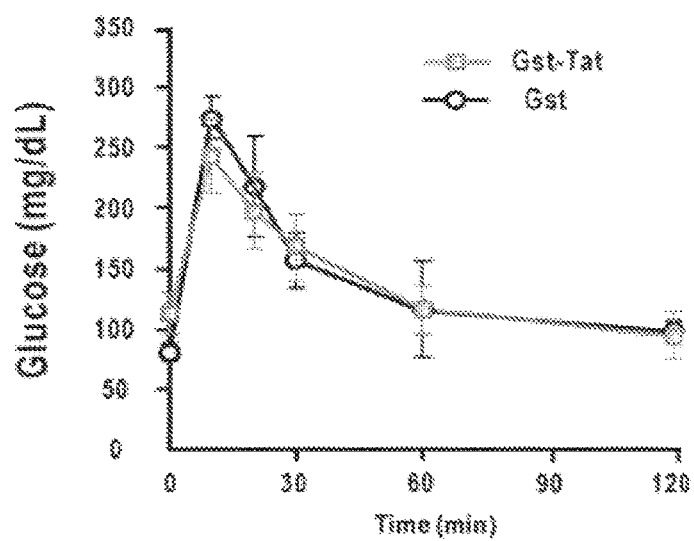
Figure 5D:
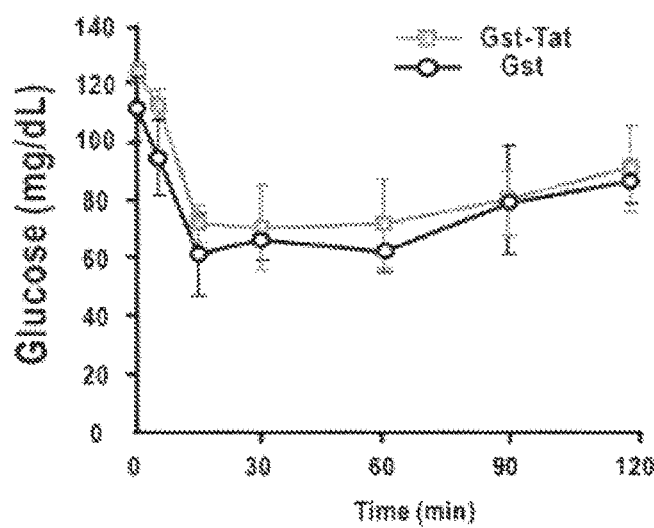
Figure 5E:
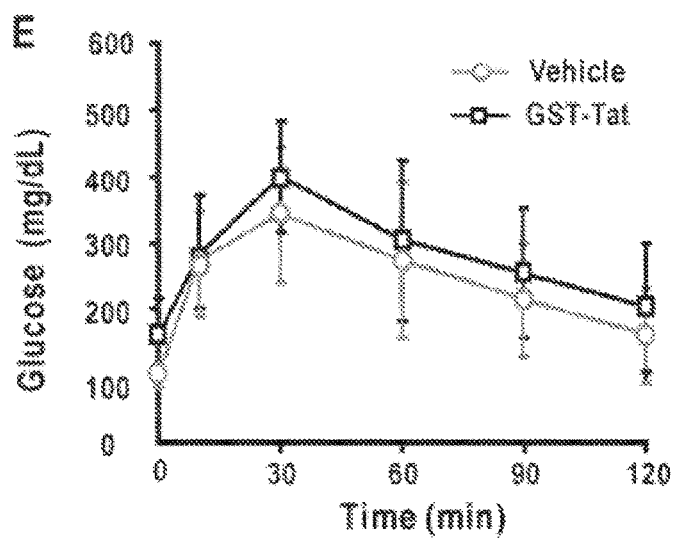
Figure 5F:
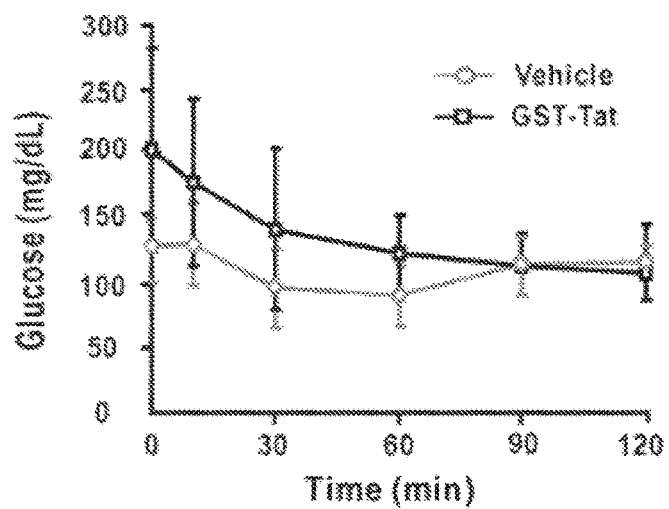

Changes in fat mass are often associated with alterations in glucose homeostasis, and are often accompanied by substantial increases in insulin resistance, hyperglycemia, and hyperinsulinemia (Lee et al., 2003). Therefore, insulin tolerance tests (ITT) and glucose tolerance tests (GTT) were performed to determine whether insulin sensitivity and glucose metabolism were altered by Tat. The rate of glucose clearance after glucose or insulin injection remained unchanged in rabbits (FIGS. 5c and 5d) and obese Lep-/- mice (FIGS. 5e and 5f) treated with Tat, suggesting that Tat did not alter glucose homeostasis, despite the reduction in fat mass.

Histology

Figure 6A:
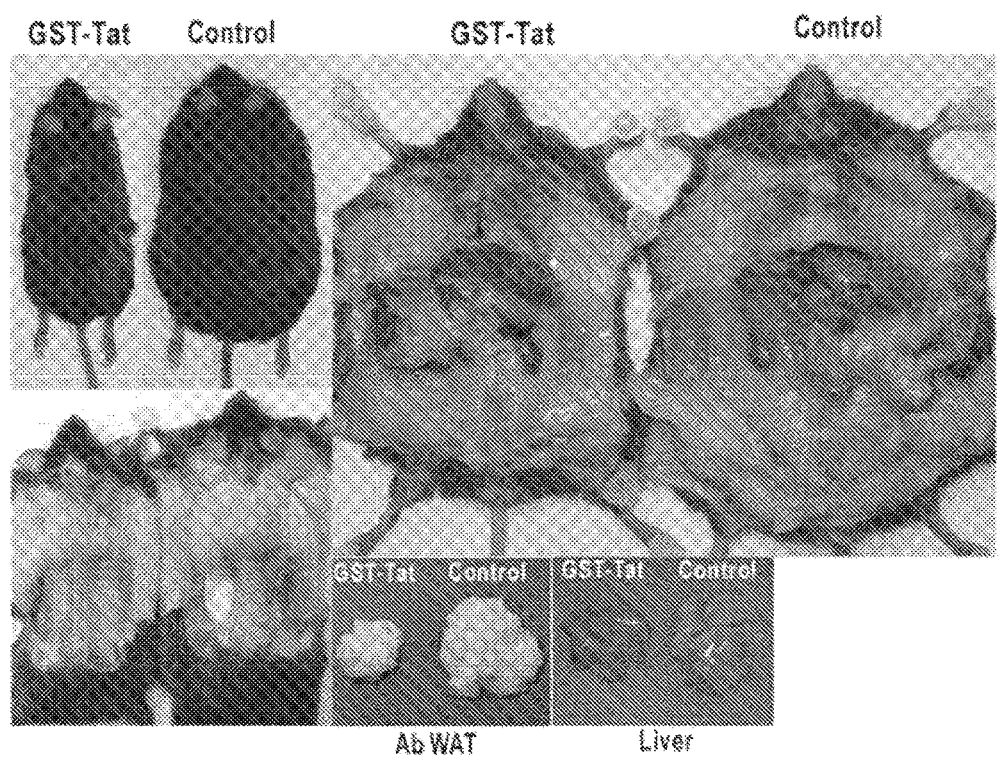
FIG. 6A and FIG. 6B, represents that Tat reduces adipose tissue mass and fat content of the liver in C57BL/6J Lep−/− mice.
Figure 6B:
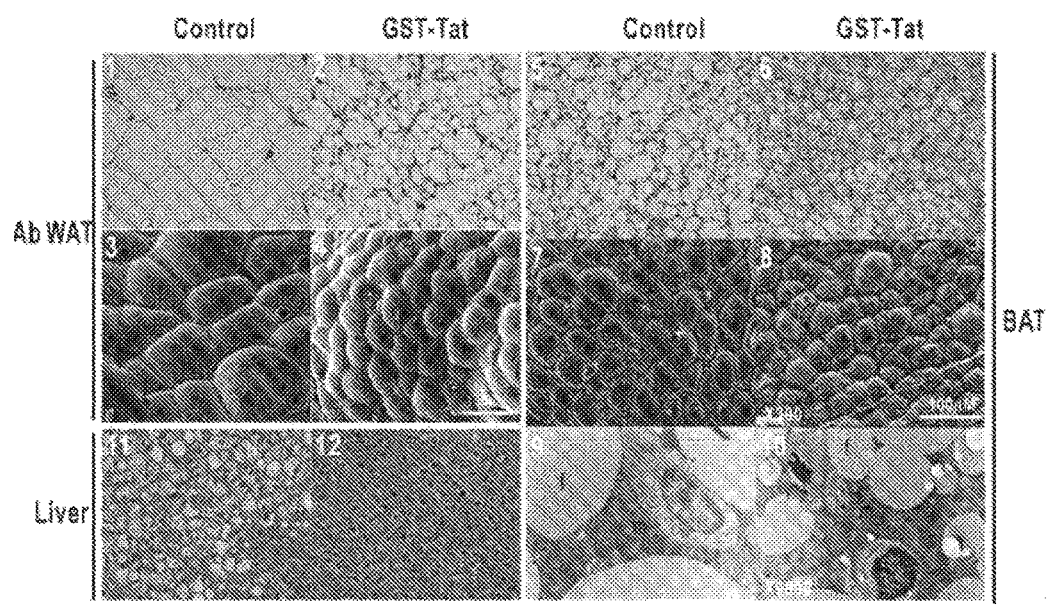

The size of the mice treated with GST-Tat for up to 49 days was greatly reduced. Dorsal and ventral views of the animal showed that various fat tissues were decreased in size. In particular, the size of abdominal fat and liver tissue was markedly reduced (FIG. 6a). H&E staining and scanning electron microscopy of the Lep-/- mice tissues treated with GST-Tat showed that the size of the adipocytes was drastically reduced and the lipids in the brown BAT and WAT were divided into much smaller droplets (FIG. 6b 1-8). The size of the WAT was nearly the same as that of BAT of untreated mice. In addition, the transmission electron microscopy showed that the cytoplasm of the BAT from Tat-treated Lep-/- mice was filled with more mitochondria. Fat content of the liver in Lep-/- mice was also significantly decreased (FIG. 6b 11, 12).

Tat Transgenic Mice Showed Reduced Fat Mass.

Figure 7A:
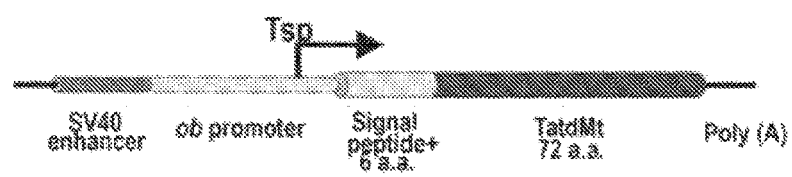
FIG. 7A through FIG. 7C, represents that FVB transgenic mice over-expressing Tat had reduced fat mass in WAT, BAT and muscle.
Figure 7B:
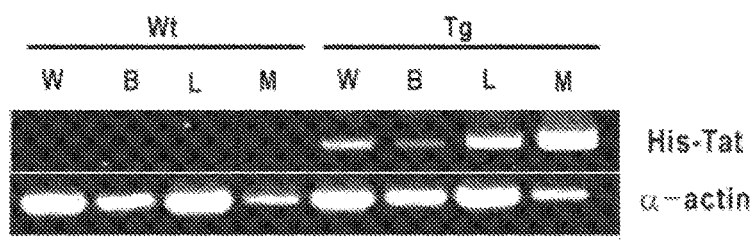
Figure 7C:
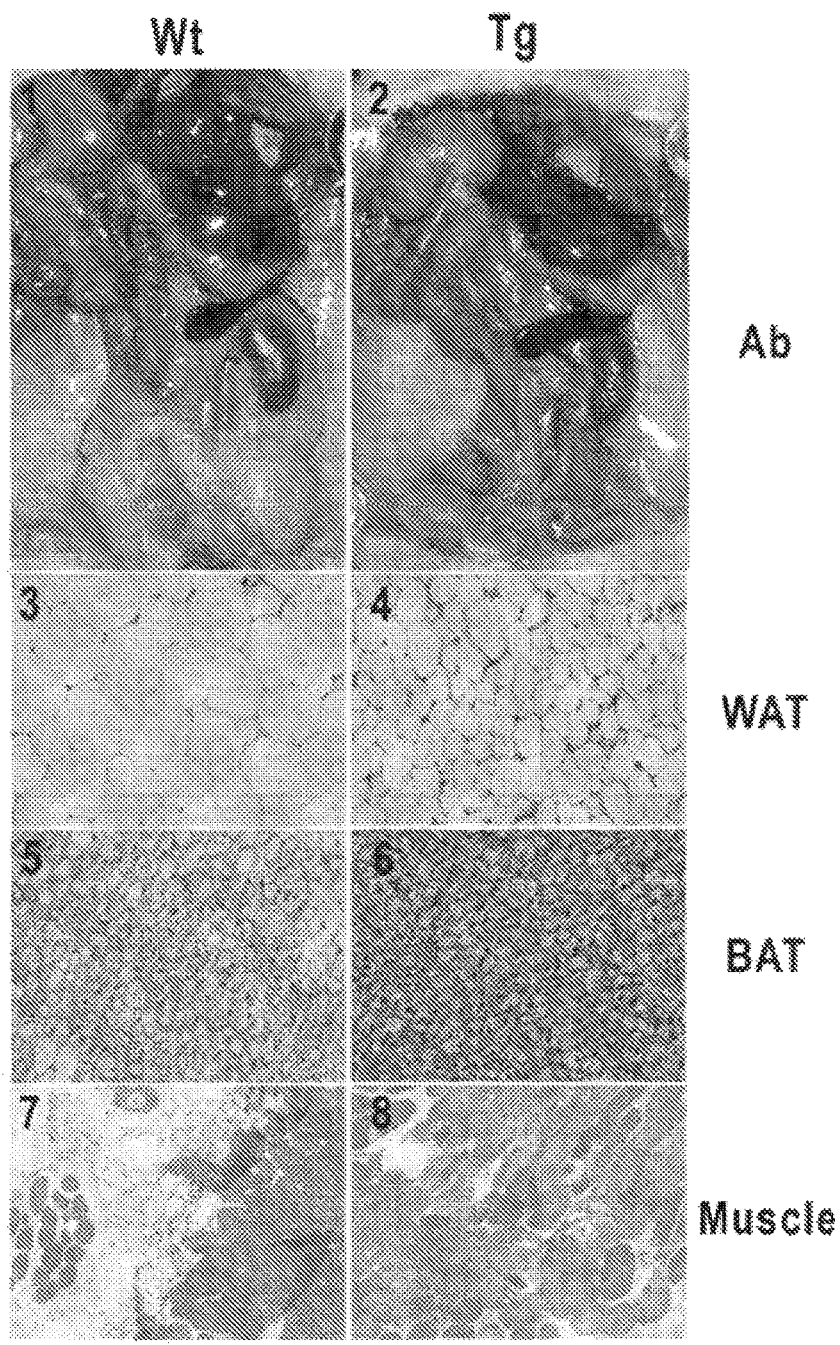

The experiment done with obese Lep-/- mice and recombinant GST-Tat fusion proteins can be potentially misleading in the study of wasting in HIV-infected individuals. This is because the physiology of obese Lep-/- mice can be different from normal mice and, in fact, few people with HIV-1 infections or AIDS are obese. Accordingly, to clearly demonstrate the function of Tat in fat tissue reduction, three transgenic FVB mouse lines over expressing Tat were generated using an expression construct, which put Tat under the control of the ob gene promoter and SV40 enhancer (FIG. 7a). RT-PCR analysis showed that the mouse expressed Tat in the WAT, BAT, liver, and muscle (FIG. 7b), an expression pattern similar to that reported for the transgenic leptin gene promoter with 762 bp upstream regulatory element (Chen et al., 1999), and showed a much lower abdominal fat content than their control littermates (FIG. 7c 1, 2). A tissue section of the transgenic mice showed that the size of the WAT was greatly reduced, and the lipid droplets in the BAT were smaller than those observed in their control littermates (FIG. 7c 3-6). Fat tissue associated with muscle fibre was markedly also reduced (FIG. 7c 7, 8).

Figure 8A:
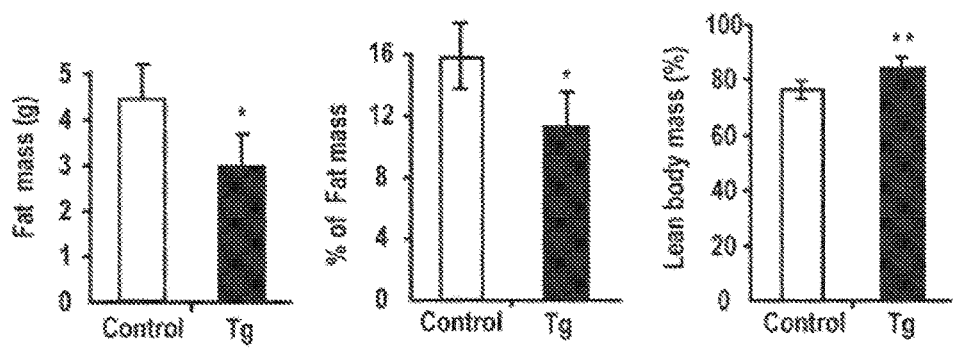
FIG. 8A shows the results of PIXImus™ mouse densitometer analysis of FAT content and lean body mass of transgenic mice. n=5. *P<0.05 versus control.

PIXImus™ x-ray mouse densitometer analysis of whole body showed that net fat mass was decreased by 34% (average 1.5 g) and the percentage of fat mass to whole body weight was decreased from 15.7 to 11.2% (FIG. 8a). Lean body mass of transgenic mice was increased by 7.8% over control littermate due to the reduction of fat mass (FIG. 8a).

The Transgenic FVB Mice Overexpressing Tat Polypeptide Showed Increased Energy Expenditure, Thermogenesis, Oxygen Consumption, and Fatty Acid β-Oxidation.

Figure 8B:
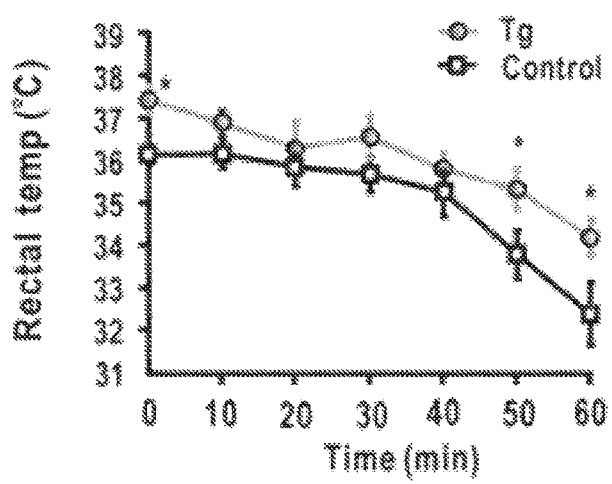
FIG. 8B shows the result of cold tolerance test at 4.degree. C. *P<0.002 versus control.
Figure 8C:
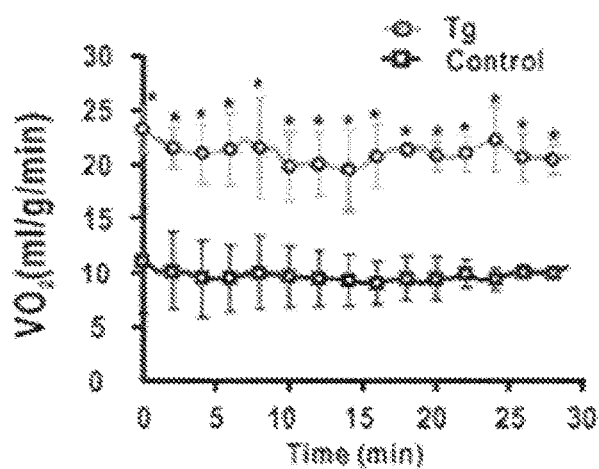
FIG. 8C shows $O_2$ consumption ($VO_2$) of control littermates and transgenic mice. *P<0.002 versus control.
Figure 8D:
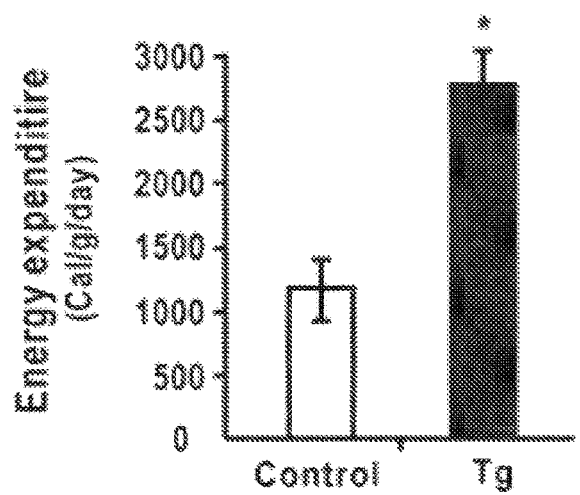
FIG. 8D indicates energy expenditure based on $VO_2$. *P<0.002 versus control.
Figure 8E:
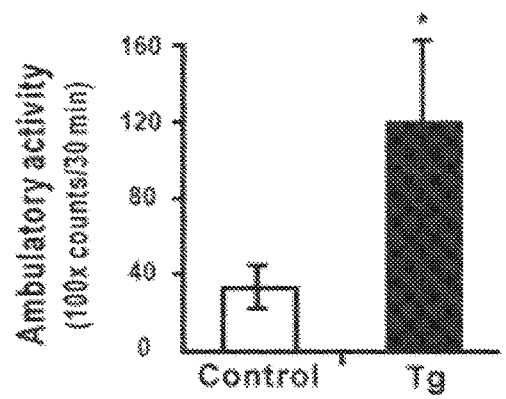
FIG. 8E shows locomotor activity. *P<0.01 versus control.
Figure 8F:
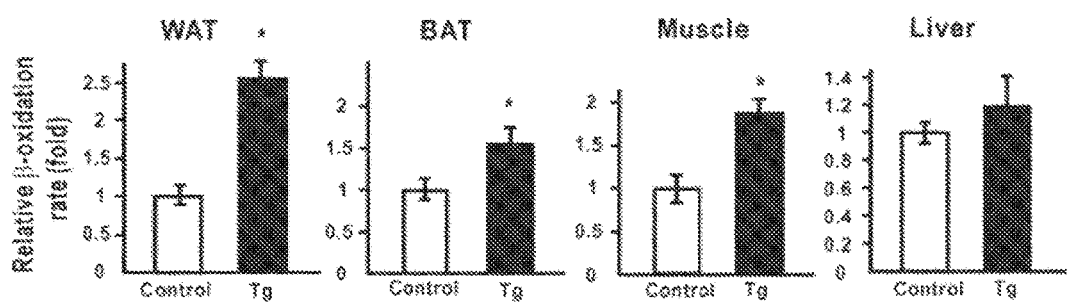
FIG. 8F shows relative fatty acid .beta.-oxidation rates in the WAT, BAT, liver, and muscle of FVB transgenic mice. Tat increases fatty acid .beta.-oxidation in WAT, BAT, and muscle. *P<0.05 versus control in WAT, BAT, and muscle. Control, control FVB littermates; Tg, transgenic FVB mice.

As in the analysis of the Tat-treated Lep-/- mice, various physiological parameters that might explain the decrease in adipose tissue mass were examined. The transgenic mice showed a 1.3° C. higher rectal temperature under normal conditions than their control littermates (FIG. 8b). This difference increased up to 1.78° C. in the 4° C. chamber at 60 min, suggesting that the Tat transgene increased thermogenesis under cold stress conditions (FIG. 8b). The animals showed a higher level of oxygen consumption (2.2× increase) and $CO_2$ output, which translated into an increase in energy expenditure (2.3× increase, which is 2,773 cal/g/day) (FIGS. 8c and 8d). The transgenic animals were very active, and showed a nearly three-fold increase in locomotor activity, suggesting that a significant amount of energy is used during physical activity (FIG. 8e). The animals also showed a significant increase in the fatty acid β-oxidation rate in the WAT (2.5-fold), BAT (1.5-fold), muscle (1.8-fold) and liver (1.2-fold) (FIG. 8f). These physiological parameters suggest that Tat fragment significantly increased the total energy expenditure (EE plus locomotor activity), utilizing the energy generated from the β-oxidation of fatty acids, particularly in BAT, WAT, and muscle. We also observed similar physiological changes in rabbits and obese Lep-/- mice (FIGS. 4 and 5) treated with GST-Tat. All animal showed increase in energy expenditure, thermogenesis, oxygen consumption, and physical activity.

Central Administration of Tat Causes Anorexia, Thermogenesis and Enhanced Energy Expenditure.

Tat protein is detected in brain mononuclear cells and in the CSF of HIV-infected individuals (Parmenter et al., 1992). The mRNA levels of Tat are also elevated in the brain of patients with HIV-related dementia (Wiley et al., 1996). Therefore, we investigated if Tat induces wasting by acting in the central nervous system (CNS). GST-Tat (0.01-0.1 nmol GST) caused a reduction in food-intake and body weight when administered intracerebroventricularly (i.c.v.) in C57BL/6J mice within 24 hrs. Single i.c.v. administration of GST-Tat (0.1 nmol) decreased food intake from 1 h post injection and the anorexigenic effects lasted for at least 24 hrs (data not shown). I.C.V. administration of a small amount of Tat could produce a significant weight reduction and anorexia, suggesting that the CNS may be a primary target site for Tat induced weight reduction and anorexia.

To investigate which part of Tat is important for the anorexic action of Tat, we compared the effect of an equal amount (0.1 nmol) of Tat and Tat fragments on food intake and body weight. Tat (a.a. 1-72) significantly reduced 24 hrs food intake and body weight. The shorter, middle fragments of Tat, Tat (a.a. 20-45) and Tat (a.a. 20-57), also showed anorexigenic effect comparable to that of Tat (a.a. 1-72). Body weight was also decreased by i.c.v. administration of Tat (a.a. 20-45) and Tat (a.a. 20-57). In contrast, C- and N-terminal fragments, Tat (a.a. 1-25) and Tat (a.a. 40-72) had no effect on body weight and food intake (FIG. 9).

Identification of Functional Domain of Tat Important in Fat Reduction; Tat (a.a. 20-45) Fragment Reduces Fat Mass in Rabbits.

Figure 10A:
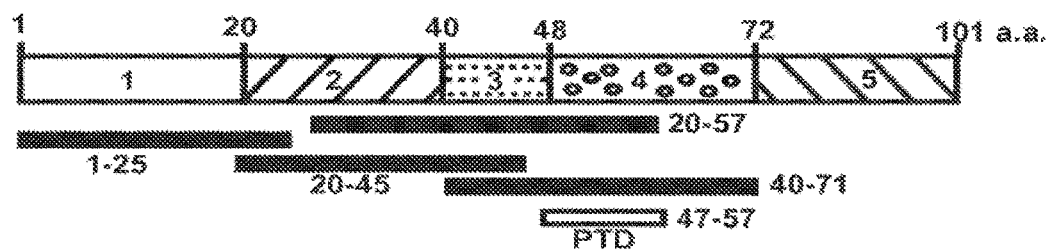
FIG. 10A through FIG. 10C, represents identification of functional domain of Tat important in fat mass reduction. Tat (a.a. 20-45) fragment reduces fat mass in rabbits.
Figure 10B:
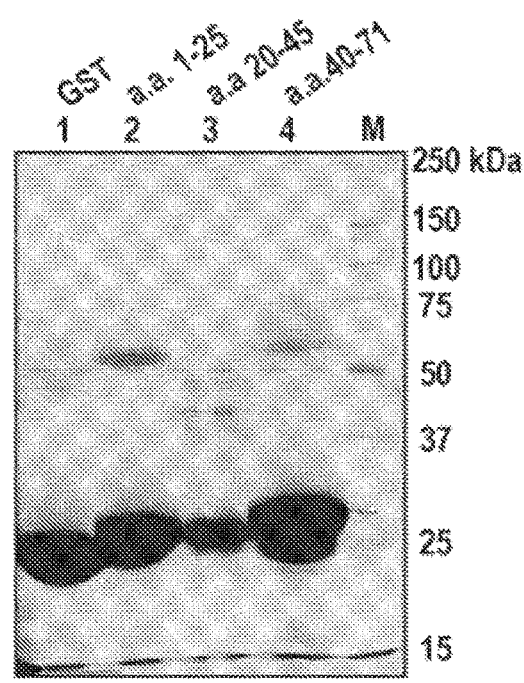
Figure 10C:
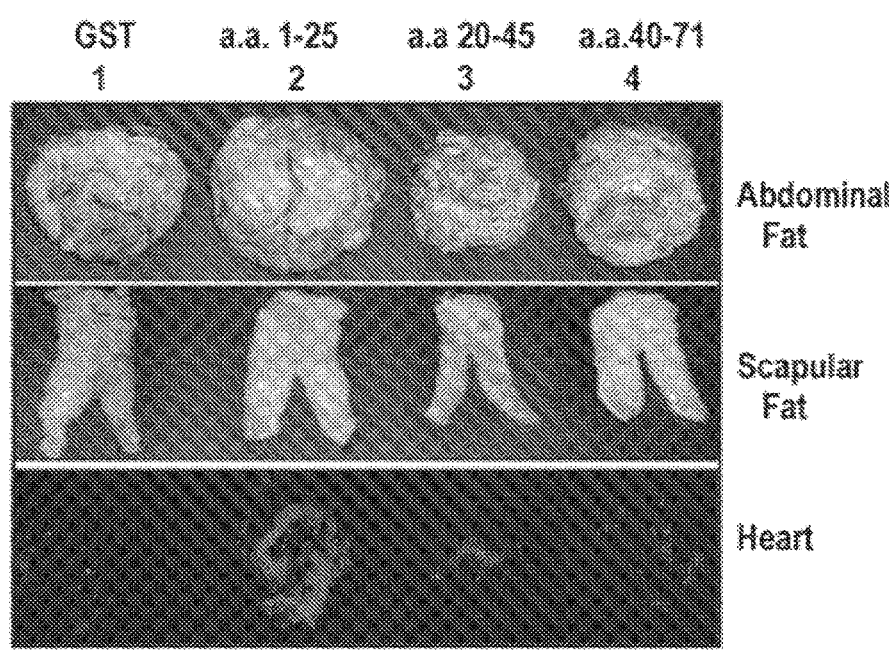

To investigate which domain of Tat is important in the reduction of fat mass in rabbits, we divided the Tat polypeptide (72 a.a. version) into three fragments, a.a. 1-25, 20-45, 40-71 (FIG. 10a). Although we also prepared Tat a.a. 24-57 and tested for central action, this particular polypeptide was not tested for fat reduction in rabbits. The cDNA fragments encoding the Tat fragments were cloned into pGEX4T expression vector and recombinant polypeptides in GST-fusion form were expressed and purified by affinity column chromatography (FIG. 10b). Rabbits were injected 4 times with two week intervals with recombinant GST or GST-Tat fragments (1 mg), subcutaneously. 10 days after final injection, rabbit tissues were analyzed for the fat mass of abdominal, scapular and heart adipose tissues in rabbits treated with various recombinant Tat polypeptides. The abdominal and scapular fat tissues isolated from the rabbit treated with Tat fragment containing a.a. 20-45 showed significantly reduced (FIG. 10c). The data suggest that the Tat (a.a. 20-45) domain is responsible for fat reducing activity of Tat polypeptide.

Changes in Gene Expression Important in Fat and Energy Metabolism.

Figure 11A:
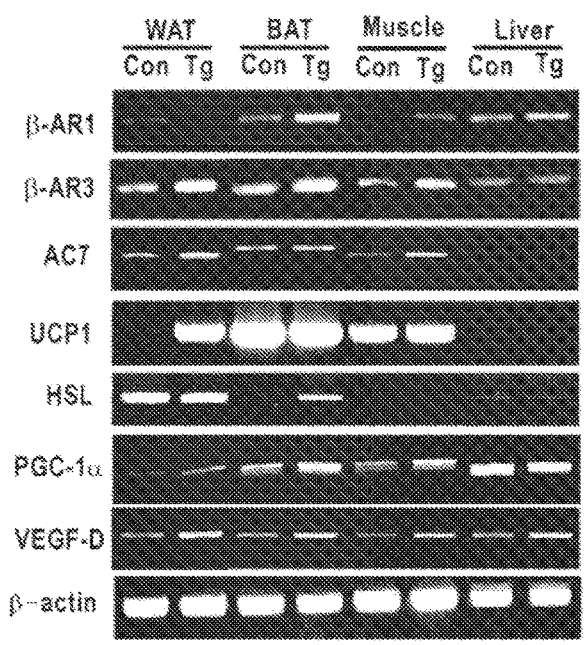
FIG. 11A through FIG. 11C, represents that Tat increases mRNA expression of .beta.-AR, UCP1, PGC-1.alpha., HSL, and also increases eNOS protein and NO, important molecules in fat metabolism or thermogenesis in peripheral tissues.
Figure 11A:
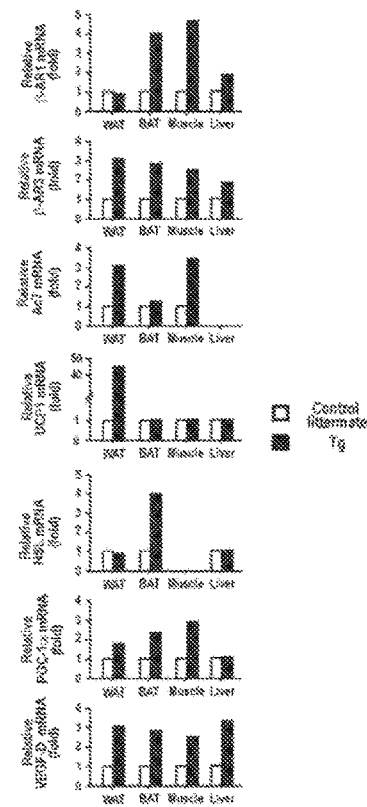
Figure 11B:
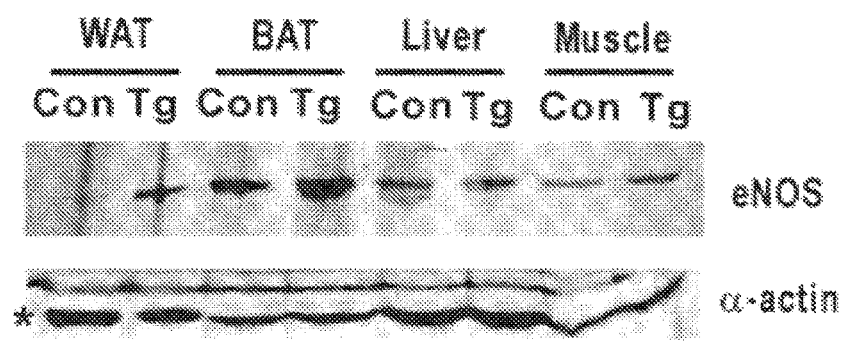

In order to understand the molecular mechanism behind the fat tissue size reduction, total RNA of the WAT, BAT, muscle, and liver was isolated from obese lep-/- mice treated with GST-Tat or GST at the end of the experiment. mRNA levels were analysed using Affymetrix microarrays and Northern blot. A confirmation of the differential expression, by RT-PCR of the total RNA from the transgenic mice, showed that Tat increased the expression of genes involved in lipid catabolism and energy expenditure. In the BAT, WAT, and muscle in Tat transgenic mice, Tat increased the mRNA levels of key molecules such as β-ARs, Ac7, UCP1, HSL, PGC-1α, and VEGF-D, which are important in lipid metabolism, thermogenesis, and lipolysis (FIG. 11a). In contrast, the liver of the Tat transgenic mice did not show a significant change in the levels of these genes that are important in energy expenditure and fat oxidation (FIG. 11b).

In the WAT, in which the principle function is to store fat, mRNA expression of β-AR3, the predominant form of the β-ARs in the adipocytes, was increased, while the other β-AR levels remained unchanged (FIG. 11a) (Collins et al. 1994; Muzzin et al. 1991). Also, mRNA expression of PGC-1α, a transcriptional coactivator important in lipid metabolism, was increased, as in the BAT and muscle. Intriguingly, mRNA expression of UCP1, which is expressed specifically in BAT and muscle, was increased dramatically in the WAT (FIG. 11a). This suggested that the WAT might have, to some extent, converted into BAT, and may have generated more heat than usual. Microscopic images of WAT showed that some of the white adipocytes were much smaller, and were comparable to the brown adipocytes. The big increase in UCP1 in WAT may be an important factor in the vastly increased energy expenditure, β-oxidation of fatty acids, and drastic WAT size reduction. mRNAs levels of adenylate cyclase 7 (AC7), a downstream molecule of β-AR, and VEGF-D were also increased, which can also contribute in lipolysis and fat oxidation (FIG. 11a).

In the BAT, which is a tissue of major energy expenditure, the mRNA levels of genes important in energy expenditure and lipolysis such as β-AR1, β-AR3, HSL, PGC-1α, UCP2, and VEGF-D were increased. This indicated that probably a similar mechanism of energy expenditure increase to WAT was involved. The HSL is important in the lipolysis of triglycerides (Londos et al., 1999). These changes may be translated into the increase in lipolysis, and energy expenditure (FIG. 11a).

In skeletal muscle, the levels of β-AR1, β-AR3, AC7, PGC-1α and VEGF-D were also increased. Accordingly, increased expression of these molecules can increase fat oxidation and energy expenditure in a similar mechanism to WAT or BAT (FIG. 11a).

Others showed that adrenergic stimulation of β-ARs increases energy expenditure and lipolysis in BAT and skeletal muscle in rodents, and that downstream molecules such as adenyl cyclase, cAMP, HSL, eNOS, NO, PGC-1α, and UCPs are activated following stimulation (Himms-Hagen, 1989; Lafontan et al., 1993; Nagase et al., 2001; Slezak et al., 2004; Solovevael., 1997). Similarly, we find that these molecules are increased in BAT, WAT and muscle of Tat-expressing transgenic mice (FIG. 11 and data not shown).

Figure 11C:
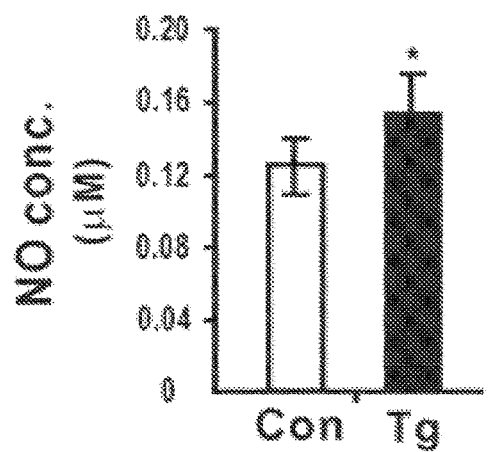

The activation of β-ARs by Tat resulted in an increase in both HSL and NO, which, in turn, can eventually cause an increase in lipolysis, fatty acid oxidation, and energy expenditure in BAT. NO was shown to be critically involved in the enhancement of thermogenic functions of BAT in rats (Saha and Kuroshima, 2000). The activation of β-ARs can be translated into an increase in eNOS and plasma NO concentration. VEGF-D, another polypeptide that can lead to increases in eNOS and NO, was also increased (Gavin et al., 2000; Ziche et al., 1997) (FIG. 11a). Accordingly, we measured the expression of nitroxide synthase (eNOS) in WAT, BAT, muscle and liver, and also the level of NO in serum. eNOS was significantly increased in lipid BAT, WAT and muscle, and NO was increased in blood serum (FIGS. 11b and 11c).

NO has been found to trigger mitochondrial biogenesis in many cell types including WAT and BAT by inducing the expression of PGC-1α, which is a master regulator of mitochondrial biogenesis (Gaudiot et al., 2000; Nisoli et al., 2003.; Saha et al., 2000). NO also plays a pivotal role in lipolysis regulation (Gaudiot et al. 1998, 2000; Penfornis and Marette. 2005; Ribiere et al., 1996). The NO generated by muscle cells may diffuse into nearby white adipocytes and cause lipolysis. The released free fatty acids may be taken up and oxidized by muscle mitochondria. This may explain the strong fatty acid β-oxidation in muscle, few adipose tissue attached with muscle (FIG. 7c 7, 8), and vigorous locomotor activity in Tat transgenic mice (FIGS. 8e and 8f). The increase in eNOS and NO, initially triggered by the increase in β-ARs and VEGF-D, may reduce the size of BAT and WAT by increasing β-oxidation and energy expenditure.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Abad, L. W., Schmitz, H. R., Parker, R., and Roubenoff. R. Cytokine Responses Differ by Compartment and Wasting Status in Patients with HIV Infection and Healthy Controls. *Cytokine* 18: 286-293 (2002).
2. Barnes, P. J., and Karin, M. Nuclear factor-kappa B: a pivotal transcription factor in chronic inflammatory diseases. *New Engl. J. Med.* 336: 1066-1071 (1997).
3. Buonaguro, L., Barillari G., Chang, H. K., Bohan, C. A., Kao, V., Morgan, R., Gallo, R. C., and Ensoli, B. Effects of the human immunodeficiency virus typefiTat protein on the expression of inflammatory cytokines. *J. Virol.* 66:7159-7167 (1992).
4. Chang, H. C., Samaniego, F., Nair, B. C., Buonaguro, L., and Ensoli, B. HIV-1 Tat protein exits from cells via a leaderless secretory pathway and binds to extracellular matrix-associated heparan sulfate proteoglycans through its basic region. *AIDS.* 11:1421-1431 (1997).
5. Chen, X. L., Hartzell, D. L., McGraw, R. A., Hausman, G. J., and Dean, R. G. Analysis of a 762 bp Proximal Leptin Promoter to Drive and Control Regulation of Transgene Expression of Growth Hormone Receptor in Mice. *Biochem. Biophys. Res. Commun.* 262 :187-192 (1999).
6. Collins, S., Daniel, K. W., Rohlfs, E. M., Ramkumar, V., Taylor, I. L., and Gettys, T. W. (1994). Impaired expression and functional activity of the beta 3- and beta1-adrenergic receptors in adipose tissue of congenitally obese (C57BL/6Job/ob) mice. *Mol. Endocrinol.* 8:518-527 (1994).
7. Conant, K., Ma, M., Nath, A., and Major, E. O. Extracellular human immunodeficiency virus type 1 Tat protein is associated with an increase in both NF-kappa B binding and protein kinase C activity in primary human astrocytes. *J. Virol.* 70: 1384-1389 (1996).
8. Cummings, D. E., and Schwartz, M. W. Melanocortins and body weight: a tale of two receptors. *Nat. Genet.* 26:8-9 (2000).
9. Fan, W., Boston, B. A., Kesterson, R. A., Hruby, V. J., and Cone, R. D. Role of melanocortinergic neurons in feeding and theagoutiobesity syndrome. *Nature.* 385:165-168 (1997).
10. Friedman, J. M., and Halaas, J. L. Leptin and the regulation of body weight in mammals. *Nature* 395:763-770. Review (1998).
11. Gaudiot, N., Jaubert, A. M., Charbonnier, E., Sabourault, D., Lacasa, D., Giudicelli, Y., and Ribiere, C. (1998). Modulation of white adipose tissue lipolysis by nitric oxide. *J. Biol. Chem.* 273:13475-13481 (1998).
12. Gaudiot, N., Ribiere, C. Jaubert, A. M., and Giudicelli, Y. Endogenous nitric oxide is implicated in the regulation of lipolysis through antioxidant-related effect. *Am. J. Physiol. Cell. Physiol.* 279: C1603-1610 (2000).
13. Gavin, T. P., Spector, D. A., Wagner, H., Breen, E. C., and Wagner, P. D. Nitric oxide synthase inhibition attenuates the skeletal muscle VEGF mRNA response to exercise. *J. Appl. Physiol.* 88:192-1198 (2000).
14. Grunfeld, C., Kotler, D. P., Shigenaga, J. K., Doerrler, W., Tierney, A., Wang, J., Pierson R. N. Jr., and Feingold, K. R. Circulating interferon-levels and hypertriglyceridemia in the acquired immunodeficiency syndrome. *Am. J. Med.* 90:154-162 (1991).
15. Grunfeld, C., and Feingold, K. R. Metabolic disturbances and wasting in the acquired immunodeficiency syndrome. *New Engl. J. Med.* 327:329-337 (1992a).
16. Grunfeld, C., Pang, M., Shimizu, L., Shigenaga, J. K., Jensen, P., and Feingold, K. R. Resting energy expenditure, caloric intake, and short-term weight change in human immunodeficiency virus infection and the acquired immunodeficiency syndrome. *Am. J. Clin. Nutr.* 55:455-460 (1992b).
17. Grunfeld, C., Pang, M., Shigenaga, J. K., Jensen, P., Lallone, R., Friedman, J., and Feingold, K. R. Serum leptin levels in the acquired immunodeficiency syndrome. *J. Clin. Endocrinol. Metab.* 81:4342-4346 (1996).
18. Himms-Hagen, J. Brown adipose tissue thermogenesis and obesity. Prog. Lipid Res. 28:67-11514 (1989).
19. Hirsch, J. The search for new ways to treat obesity. *Proc. Natl. Acad. Sci. USA.* 99:9096-9067 (2002).
20. Huang, Q. H., Hruby, V. J., and Tatro, J. B. Role of central melanocortins in endotoxin-induced anorexia. *Am. J. Hruby,* V.J6, (3Pt2), R864-R871 (1999).
21. Huszar, D., Lynch, C. A., Fairchild-Huntress, V., Dunmore, J. H., Fang, Q., Berkemeier, L. R., Gu, W., Kesterson, R. A., Boston, B. A., Cone, R. D., Smith, F. J., Campfield, L. A., Burn, P., and Lee, F. Targeted disruption of the melanocortin-4 receptor results in obesity in mice. *Cell* 88:131-141 (1997).
22. Jeang, K. T., Xiao, H., and Rich, E. A. Multifaceted activities of the HIV-1 transactivator of transcription, Tat. *J. Biol. Chem.* 274: 28837-28840. Review (1999).
23. Koenig, S., Gendelman, H. E., Orenstein, J. M., Dal Canto, M. C., Pezeshkpour, G. H., and Yungbluth, M. Detection of AIDS virus in macrophages in brain tissue from AIDS patients with encephalopathy. *Science* 233: 1089-1093 (1986).
24. Krude, H., Biebermann, H., Luck, W., Horn, R., Brabant, G., and Gruters, A. Severe early-onsetobesity, adrenalin sufficiency and red hair pigmentation caused by POMC mutations in humans. *Nat. Genet.* 19:155-157 (1998).
25. Lafontan, M., and Berlan, M. M. Fat cell adrenergic receptors and the control of white and brown fat cell function. *J. Lipid. Res.* 34:1057-1091 (1993).
26. Lee, K., Villena, J. A., Moon, Y. S, Kim, K. H., Lee, S., Kang, C., and Sul, H. S. Inhibition of adipogenesis and development of glucose intolerance by soluble preadipocyte factor-1 (Pref-1). *J. Clin. Invest.* 111:453-461 (2003).
27. Li, J. C., Lee, D. C., Cheung, B. K., and Lau, A. S. Mechanisms for HIV Tat upregulation of IL-10 and other cytokine expression: kinase signaling and PKR-mediated immune response. *FEBS Lett.* 579: 3055-3062 (2005).

28. Londos, C., Brasaemle, D. L., Schultz, C. J., Adler-Wailes, D. C., Levin, D. M., Kimmel, A. R., and Rondinone, C. M. On the control of lipolysis in adipocytes. *Ann. N.Y. Acad. Sci.* 892:155-168 (1999).
29. Macallan, D. C., Noble, C., Baldwin, C., Foskett, M., McManus, T., and Griffin, G. E. Prospective analysis of patterns of weight change in stage IV human immunodeficiency virus infection. *Am. J. Clin. Nutr.* 58:417-424 (1993).
30. Macallan, D. C., Noble, C., Baldwin, C., Jebb, S. A., Prentice, A. M., Coward, W. A., Sawyer, M. B., McManus, T. J., and Griffin, G. E. Energy expenditure and wasting in human immunodeficiency virus infection. *New Engl. J. Med.* 333:83-88 (1995).
31. Magnuson, D. S. K., Knudsen, B. E., Geiger, J. D., Brownstone, R. M., and Nath, A. Human immunodeficiency virus type 1 tat activates non-N-methyl-D-aspartate excitator R.mino aci., aceptors and causes neurotoxicity. *Ann Neurol.* 37: 373-380 (1995).
32. Min, J. K., Kim, Y. M., Kim, S. W., Kwon, M. C., Kong, Y. Y., Hwang, I. K., Won, M. H., Rho, J., and Kwon, Y. G. TNF-Related Activation-Induced Cytokine Enhances Leukocyte Adhesiveness: Induction of ICAM-1 and VCAM-1 via TNF Receptor-Associated Factor and Protein Kinase C-Dependent NF-kB Activation in Endothelial Cells. *J. Immunol.* 175:531-540 (2005).
33. Mulligan, K., and Schambelan, M. An abolic treatment with GH,IGF-I, or anabolic steroids in patients with HIV-associated wasting. *Int. J. Cardiol.* 85: 151-159. Review (2002).
34. Muzzin, P., Revelli, J. P., Kuhne, F. Gocayne, J. D., McCombie, W. R., Venter, J. C., Giacobino, J. P., and Fraser, C. M. An adipose tissue-specific beta-adrenergic receptor. Molecular cloning and down-regulation in obesity. *J. Biol. Chem.* 266: 24053-24058 (1991).
35. Myers, G., Korber, B. T., Foley, B. T., Jeang, K.-T., Mellors, J. W., and Wain-Hobson, S. Theoretical biology and biophysics group, Los Alamos National Laboratory, Los Alamos, N. Mex. pp. III-11-III-26. [Online.] http://www.unaids.org (1996).
36. Nagase, I., Yoshida, T., and Saito, M. Up-regulation of uncoupling proteins by b-adrenergic stimulation in L6 myotubes. *FEBS Lett.* 494: 175-180 (2001).
37. Nath, A., Psooy, K., Martin, C., Knudsen, B., Magnuson, D. S., Haughet, N., and Geiger, J. D. Identification of a human immunodeficiency virus type 1 Tat epitope that is neuroexcitatory and neurotoxic. *J. Virol.* 70: 1475-1480 (1996).
38. Nisoli, E., Clementi, E., Paolucci, C., Cozzi, V., Tonello, C., Sciorati, C., Bracale, R., Valerio, A., Francolini, M., Moncada, S., and Carruba, M. O. Mitochondrial biogenesis in mammals: the role of endogenous nitric oxide. *Science* 299: 896-899 (2003).
39. Otake, K., Omoto, S., Yamamoto, T., Okuyama, H., Okada, H., Okada, N., Kawai, M., Saksena, N. K., and Fujii Y. R. HIV-1 Nef protein in the nucleus influences adipogenesis as well as viral transcription through the peroxisome proliferator-activated receptors. *AIDS* 18: 189-198 (2004).
40. Parmenter, H. K., van Wichen, D. F, Meyling, F. H., Goudsmit, J., and Schuurman, H. J. Epitopes of human immunodeficiency virus regulatory proteins tat, nef, and rev are expressed in normal human tissue. *Am. J. Pathol.* 141:1209-1216 (1992).
41. Penfornis, P., and Marette, A. Inducible nitric oxide synthase modulates lipolysis in adipocytes. *J. Lipid Res.* 46:135-142 (2005).
42. Probst, J. C., Jirikowski. G. F., Skutella. T., and Vedder. H. Rat hypothalamus neuron-like cells in primary culture accumulate and translate mRNA coding for the amphibian P-domain peptide xP1. *Cell. Mol. Neurobiol.* 17: 333-40 (1997).
43. Puigserver, P., Rhee, J., Lin, J., Wu, Z., Yoon, J.C., Zhang, C. Y., Krauss, S., Mootha, V. K., Lowell, B. B., and Spiegelman. B. M. Cytokine stimulation of energy expenditure through p38 MAP kinase activation of PPAR coactivator-1. *Mol. Cell.* 8: 971-982 (2001).
44. Rautonen, J., Rautonen, N., Martin, N. L., and Wara, D. W. HIV type 1 Tat protein induces immunoglobulin and interleukin 6 synthesis by uninfected peripheral blood mononuclear cells. *AIDS Res Hum Retroviruses.* 10: 781-785 (1994).
45. Ribiere, C., Jaubert, A. M., Gaudiot, N., Sabourault, D., Marcus, M. L., Boucher, J. L., Denis-Henriot, D., and Giudicelli, Y. White adipose tissue nitric oxide synthase: a potential source for NO production. *Biochem Biophys Res Commun.* 222: 706-712 (1996).
46. Saha, S. K., and Kuroshima A. S. Nitric oxide and thermogenic function of brown adipose tissue in rats. *Jpn. J. Physiol.* 50: 337-342 (2000).
47. Satoh, N., Ogawa, Y., Katsuura, G., Numata, Y., Masuzaki, H., Yoshimasa, Y., and Nakao, K. Satiety effect and sympathetic activation of leptin are mediated by hypothalamic melanocortin system. *Neurosci Lett.* 249:107-110 (1998).
48. Schwartz, M. W., Woods, S. C., Seeley, R. J., and Baskin, D. G. Central nervous system control of food intake. *Nature* 404: 661-671 (2000).
49. Schölzke, M. N., Potrovita, I., Subramaniam, S., Prinz, S., and Schwaninger, M. Glutamate activates NF-kB through calpain in neurons. *Eur. J. Neuro.* 18: 3305-3310 (2003).
50. Slezak, J., Buchwalow, I. B., Schulze, W., Karczewski, P., Wallukat, G., Samoilova, V. E., Krause, E. G., Neumann, J., and Haller, H. Cellular control of nitric oxide synthase expression and activity in rat cardiomyocytes. *Antioxid Redox Signal.* 6: 345-352 (2004).
51. Soloveva, V., Graves, R. A. Rasenick. M. M. Spiegelman, B. M. and Ross, S. R. Transgenic mice overexpressing the β1-adrenergic receptor in adipose tissue are resistant to obesity. *Mol. Endocrinol.* 11: 27-38 (1997).
52. Wiley, C. A., Baldwin, M., and Achim, C. L. Expression of HIV regulatory and structural mRNA in the central nervous system. *AIDS* 10: 843-847 (1996).
53. Yarasheski, K. E., Zachwieja, J. J., Horgan, M. M., Powderly, W. G., Santiago, J. V., and Landt, M. Serum leptin concentrations in human immunodeficiency virus-infected men with low adiposity. *Metabolism* 46: 303-305 (1997).
54. Jiang, Z., Zamanian-Daryoush, M., Nie, H., Silva, A. M., Williams, B. R., and Li, X. Poly(I-C)-induced Toll-like receptor 3 (TLR3)-mediated activation of NF-kappa B and MAP kinase is through an interleukin-1 receptor-associated kinase (IRAK)-independent B anwaion Bloying the signaling components TLR3-TRAF6-TAK1-TAB2-PKR. *J. Biol. Chem.* 278: 16713-16719 (2003).
55. Vaisse, C., Clement, K., Guy G. B., and Froguel, P. A frameshift mutation in human MC4R is associated with a dominant form of obesity. *Nat. Genet.* 20: 113-114 (1998).
56. Ziche, M., Morbidelli, L., Choudhuri, R., Zhang, H. T., Donnini, S., Granger, H. J., and Bicknell, R. Nitric oxide synthase lies downstream from vascular endothelial growth factor-induced but not basic fibroblast growth factor-induced angiogenesis. *J. Clin. Invest.* 99: 2625-2534 (1997).

What is claimed is:

1. A method of alleviating or treating obesity in a subject in need thereof, the method comprising administering to the subject a composition comprising at least one of the group consisting of a peptide consisting of the amino acid sequence of SEQ ID NO: 1 and a peptide consisting of the amino acid sequence of SEQ ID NO:2, wherein after administration of the composition, the subject's obesity is alleviated or treated.

2. The method of claim 1, wherein the composition is a pharmaceutical composition.

3. The method of claim 1, wherein the subject is human.

4. A method of reducing adipose tissue in a subject in need thereof, the method comprising administering to the subject a composition comprising at least one of the group consisting of a peptide consisting of the amino acid sequence of SEQ ID NO: 1 and a peptide consisting of the amino acid sequence of SEQ ID NO:2, wherein after administration of the composition, the subject's adipose tissue is reduced.

5. The method of claim 4, wherein the composition is a pharmaceutical composition.

6. The method of claim 4, wherein the subject is human.

7. A method of increasing energy expenditure in a subject in need thereof, the method comprising administering to the subject a composition comprising at least one of the group consisting of a peptide consisting of the amino acid sequence of SEQ ID NO: 1 and a peptide consisting of the amino acid sequence of SEQ ID NO:2, wherein after administration of the composition, energy expenditure in the subject is increased.

8. The method of claim 7, wherein the composition is a pharmaceutical composition.

9. The method of claim 7, wherein the subject is human.

* * * * *

SEQUENCE LISTING

<160> NUMBER OF SEQ ID NOS: 26

<210> SEQ ID NO 1
<211> LENGTH: 26
<212> TYPE: PRT
<213> ORGANISM: Human immunodeficiency virus type 1

<400> SEQUENCE: 1

Thr Ala Cys Thr Asn Cys Tyr Cys Ala Lys Cys Cys Phe His Cys Gln
1               5                   10                  15

Val Cys Phe Ile Thr Lys Ala Leu Gly Ile
            20                  25

<210> SEQ ID NO 2
<211> LENGTH: 38
<212> TYPE: PRT
<213> ORGANISM: Human immunodeficiency virus type 1

<400> SEQUENCE: 2

Thr Ala Cys Thr Asn Cys Tyr Cys Ala Lys Cys Cys Phe His Cys Gln
1               5                   10                  15

Val Cys Phe Ile Thr Lys Ala Leu Gly Ile Ser Tyr Gly Arg Ala Lys
            20                  25                  30

Arg Arg Gln Arg Arg Arg
        35

<210> SEQ ID NO 3
<211> LENGTH: 78
<212> TYPE: DNA
<213> ORGANISM: Human immunodeficiency virus type 1

<400> SEQUENCE: 3
actgcttgta ccaattgcta ttgtggaaag tgttgctttc attgccaagt ttgtttcata     60
acaaaagcct taggcatc                                                  78

<210> SEQ ID NO 4
<211> LENGTH: 114
<212> TYPE: DNA
<213> ORGANISM: Human immunodeficiency virus type 1

<400> SEQUENCE: 4
actgcttgta ccaattgcta ttgtggaaag tgttgctttc attgccaagt ttgtttcata     60
acaaaagcct taggcatctc ctatggcagg gcaaagcgga cagcgacg aaga           114

<210> SEQ ID NO 5
<211> LENGTH: 38
<212> TYPE: DNA
<213> ORGANISM: Artificial Sequence
<220> FEATURE:
<223> OTHER INFORMATION: Forward primer used in RT-PCR of the mRNAs
      involved in lipid catabolism and energy expenditure  (beta-AR 1)

<400> SEQUENCE: 5
gatcgaattc aaccatgggc gcggggcgc tcgccctg                              38

<210> SEQ ID NO 6
<211> LENGTH: 35
<212> TYPE: DNA

```
<213> ORGANISM: Artificial Sequence
<220> FEATURE:
<223> OTHER INFORMATION: Reverse primer used in RT-PCR of the mRNAs
      involved in lipid catabolism and energy expenditure  (beta-AR 1)

<400> SEQUENCE: 6
gatcctcgag ctggtagcga aagggcgacg tgatg                                 35

<210> SEQ ID NO 7
<211> LENGTH: 38
<212> TYPE: DNA
<213> ORGANISM: Artificial Sequence
<220> FEATURE:
<223> OTHER INFORMATION: Forward primer used in RT-PCR of the mRNAs
      involved in lipid catabolism and energy expenditure (beta-AR2)

<400> SEQUENCE: 7
gatcgaattc aaccatgggg ccacacggga acgacagc                              38

<210> SEQ ID NO 8
<211> LENGTH: 35
<212> TYPE: DNA
<213> ORGANISM: Artificial Sequence
<220> FEATURE:
<223> OTHER INFORMATION: Reverse primer used in RT-PCR of the mRNAs
      involved in lipid catabolism and energy expenditure (beta-AR2)

<400> SEQUENCE: 8
gatcctcgag caaaaaggag gtaaggccag ataca                                 35

<210> SEQ ID NO 9
<211> LENGTH: 38
<212> TYPE: DNA
<213> ORGANISM: Artificial Sequence
<220> FEATURE:
<223> OTHER INFORMATION: Forward Primer used in RT-PCR of the mRNAs
      involved in lipid catabolism and energy expenditure (beta-AR3)

<400> SEQUENCE: 9
gatcgaattc aaccatggct ccgtggcctc acagaaac                              38

<210> SEQ ID NO 10
<211> LENGTH: 35
<212> TYPE: DNA
<213> ORGANISM: Artificial Sequence
<220> FEATURE:
<223> OTHER INFORMATION: Reverse primer used in RT-PCR of the mRNAs
      involved in lipid catabolism and energy expenditure (beta-AR3)

<400> SEQUENCE: 10
gatcctcgag aaaggacacg gcagcggaca cgatc                                 35

<210> SEQ ID NO 11
<211> LENGTH: 24
<212> TYPE: DNA
<213> ORGANISM: Artificial Sequence
<220> FEATURE:
<223> OTHER INFORMATION: Forward Primer used in RT-PCR of the mRNAs
      involved in lipid catabolism and energy expenditure (AC7)

<400> SEQUENCE: 11
gccaaggggc gctacttcct aaat                                             24

<210> SEQ ID NO 12
<211> LENGTH: 24
<212> TYPE: DNA
<213> ORGANISM: Artificial Sequence
```

```
<220> FEATURE:
<223> OTHER INFORMATION: Reverse Primer used in RT-PCR of the mRNAs
      involved in lipid catabolism and energy expenditure (AC7)

<400> SEQUENCE: 12
aaggctcttg tcacagctcc aaac                                              24

<210> SEQ ID NO 13
<211> LENGTH: 38
<212> TYPE: DNA
<213> ORGANISM: Artificial Sequence
<220> FEATURE:
<223> OTHER INFORMATION: Forward Primer used in RT-PCR of the mRNAs
      involved in lipid catabolism and energy expenditure (HSL)

<400> SEQUENCE: 13
gatcgaattc aaccatggat ttacgcacga tgacacag                               38

<210> SEQ ID NO 14
<211> LENGTH: 35
<212> TYPE: DNA
<213> ORGANISM: Artificial Sequence
<220> FEATURE:
<223> OTHER INFORMATION: Reverse Primer used in RT-PCR of the mRNAs
      involved in lipid catabolism and energy expenditure (HSL)

<400> SEQUENCE: 14
gatcctcgag gcggccgtag aagcagcctt tgtgt                                  35

<210> SEQ ID NO 15
<211> LENGTH: 24
<212> TYPE: DNA
<213> ORGANISM: Artificial Sequence
<220> FEATURE:
<223> OTHER INFORMATION: Forward Primer used in RT-PCR of the mRNAs
      involved in lipid catabolism and energy expenditure (VEGF-D)

<400> SEQUENCE: 15
atgtgtggag aatggggaat gggg                                              24

<210> SEQ ID NO 16
<211> LENGTH: 24
<212> TYPE: DNA
<213> ORGANISM: Artificial Sequence
<220> FEATURE:
<223> OTHER INFORMATION: Reverse Primer used in RT-PCR of the mRNAs
      involved in lipid catabolism and energy expenditure (VEGF-D)

<400> SEQUENCE: 16
gagatgtagg aggtgcttgt gttc                                              24

<210> SEQ ID NO 17
<211> LENGTH: 38
<212> TYPE: DNA
<213> ORGANISM: Artificial Sequence
<220> FEATURE:
<223> OTHER INFORMATION: Forward Primer used in RT-PCR of the mRNAs
      involved in lipid catabolism and energy expenditure (PGC-1alpha)

<400> SEQUENCE: 17
gatcgaattc aaccatggct tgggacatgt gcagccaa                               38

<210> SEQ ID NO 18
<211> LENGTH: 35
<212> TYPE: DNA
<213> ORGANISM: Artificial Sequence
<220> FEATURE:
```

```
<223> OTHER INFORMATION: Reverse Primer used in RT-PCR of the mRNAs
      involved in lipid catabolism and energy expenditure (PGC-1alpha)

<400> SEQUENCE: 18
gatcctcgag atggttctga gtgctaagac cgctg                               35

<210> SEQ ID NO 19
<211> LENGTH: 36
<212> TYPE: DNA
<213> ORGANISM: Artificial Sequence
<220> FEATURE:
<223> OTHER INFORMATION: Forward Primer used in RT-PCR of the mRNAs
      involved in lipid catabolism and energy expenditure (UCP 1)

<400> SEQUENCE: 19
gatcgaattc aaccatggtg aacccgacaa cttccg                              36

<210> SEQ ID NO 20
<211> LENGTH: 34
<212> TYPE: DNA
<213> ORGANISM: Artificial Sequence
<220> FEATURE:
<223> OTHER INFORMATION: Reverse Primer used in RT-PCR of the mRNAs
      involved in lipid catabolism and energy expenditure (UCP 1)

<400> SEQUENCE: 20
gatcctcgag ttatgtggta caatccactg tctg                                34

<210> SEQ ID NO 21
<211> LENGTH: 36
<212> TYPE: DNA
<213> ORGANISM: Artificial Sequence
<220> FEATURE:
<223> OTHER INFORMATION: Forward Primer used in RT-PCR of the mRNAs
      involved in lipid catabolism and energy expenditure (UCP 2)

<400> SEQUENCE: 21
gatcgaattc aaccatggtt ggtttcaagg ccacag                              36

<210> SEQ ID NO 22
<211> LENGTH: 34
<212> TYPE: DNA
<213> ORGANISM: Artificial Sequence
<220> FEATURE:
<223> OTHER INFORMATION: Reverse Primer used in RT-PCR of the mRNAs
      involved in lipid catabolism and energy expenditure (UCP 2)

<400> SEQUENCE: 22
gatcctcgag tcagaaaggt gcctcccgag attg                                34

<210> SEQ ID NO 23
<211> LENGTH: 39
<212> TYPE: DNA
<213> ORGANISM: Artificial Sequence
<220> FEATURE:
<223> OTHER INFORMATION: Forward Primer used in RT-PCR of the mRNAs
      involved in lipid catabolism and energy expenditure (UCP 3)

<400> SEQUENCE: 23
gatcgaattc aaccatggtt ggacttcagc cctccgaag                           39

<210> SEQ ID NO 24
<211> LENGTH: 35
<212> TYPE: DNA
<213> ORGANISM: Artificial Sequence
<220> FEATURE:
<223> OTHER INFORMATION: Reverse Primer used in RT-PCR of the mRNAs
``` involved in lipid catabolism and energy expenditure (UCP 3)

<400> SEQUENCE: 24
gatcctcgag tcaaaacgga gattcccgca gtacc                35

<210> SEQ ID NO 25
<211> LENGTH: 37
<212> TYPE: DNA
<213> ORGANISM: Artificial Sequence
<220> FEATURE:
<223> OTHER INFORMATION: Forward Primer used in RT-PCR of the mRNAs
      involved in lipid catabolism and energy expenditure (COXII)

<400> SEQUENCE: 25
gatcgaattc accatggcct acccattcca acttggt              37

<210> SEQ ID NO 26
<211> LENGTH: 34
<212> TYPE: DNA
<213> ORGANISM: Artificial Sequence
<220> FEATURE:
<223> OTHER INFORMATION: Reverse Primer used in RT-PCR of the mRNAs
      involved in lipid catabolism and energy expenditure (COXII)

<400> SEQUENCE: 26
gatcctcgag ttaaattatt gaagcagatc agtt                 34